(12) United States Patent
Funk et al.

(10) Patent No.: US 11,203,014 B2
(45) Date of Patent: Dec. 21, 2021

(54) METHODS FOR COLLECTING BIOLOGICAL SAMPLES FOR QUANTIFYING HEAVY METALS

(71) Applicant: Northwestern University, Evanston, IL (US)

(72) Inventors: William E. Funk, Evanston, IL (US); Thomas W. McDade, Evanston, IL (US); Andrew Unger, Bethlehem, PA (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/532,336

(22) Filed: Aug. 5, 2019

(65) Prior Publication Data

US 2020/0238275 A1     Jul. 30, 2020

Related U.S. Application Data

(63) Continuation of application No. 15/602,864, filed on May 23, 2017, now Pat. No. 10,369,564, which is a
(Continued)

(51) Int. Cl.
*C12Q 1/00* (2006.01)
*B01L 3/00* (2006.01)
(Continued)

(52) U.S. Cl.
CPC ............ *B01L 3/5023* (2013.01); *A61B 5/151* (2013.01); *A61B 5/150022* (2013.01); *A61B 5/15105* (2013.01); *A61B 5/15142* (2013.01); *A61B 5/150305* (2013.01); *A61B 5/150358* (2013.01); *A61B 5/150755* (2013.01); *B01L 3/5055* (2013.01); *G01N 33/84* (2013.01);

*A61B 5/150412* (2013.01); *A61B 5/150503* (2013.01); *B01L 1/52* (2019.08); *B01L 2200/0689* (2013.01); *B01L 2200/141* (2013.01); *B01L 2200/185* (2013.01); *B01L 2300/021* (2013.01); *B01L 2300/069* (2013.01);
(Continued)

(58) Field of Classification Search
CPC ................................................. C12Q 2454/114
See application file for complete search history.

(56) References Cited

U.S. PATENT DOCUMENTS 3,443,903 A    5/1969  Haack
4,771,631 A    9/1988  Lehitkoski
(Continued)

FOREIGN PATENT DOCUMENTS

GB         1073181        6/1967

OTHER PUBLICATIONS

Al-Saleh I, et al (2011) Heavy metals (lead, cadmium and mercury) in maternal, cord blood and placenta of healthy women. Int J Hyg Environ Health 214: 79-101.
(Continued)

*Primary Examiner* — Rosanne Kosson
(74) *Attorney, Agent, or Firm* — Quarles & Brady LLP

(57) ABSTRACT

Disclosed are devices, kits, compositions, and methods for collecting, transporting, and detecting toxicants, pathogens, and biomarkers in a biological sample. The devices, kits, compositions and methods may be utilized to collect and transport dried blood samples from a skin prick and detect toxicants, pathogens, and biomarkers in the dried blood samples.

19 Claims, 24 Drawing Sheets

Related U.S. Application Data continuation-in-part of application No. 14/778,234, filed as application No. PCT/US2014/028146 on Mar. 14, 2014, application No. 16/532,336, which is a continuation of application No. 15/602,864, filed on May 23, 2017, now Pat. No. 10,369,564.

(60) Provisional application No. 61/803,674, filed on Mar. 20, 2013, provisional application No. 62/340,261, filed on May 23, 2016.

(51) Int. Cl.

| | |
|---|---|
| G01N 33/84 | (2006.01) |
| A61B 5/151 | (2006.01) |
| A61B 5/15 | (2006.01) |
| B01L 1/00 | (2006.01) |

(52) U.S. Cl.
CPC ............ B01L 2300/0681 (2013.01); B01L 2300/0816 (2013.01); B01L 2300/126 (2013.01)

(56) References Cited

U.S. PATENT DOCUMENTS

| | | | |
|---|---|---|---|
| 5,427,953 | A | 6/1995 | Yee |
| 7,407,578 | B2 | 8/2008 | Sakaino |
| 7,569,184 | B2 | 8/2009 | Wandell |
| 7,926,661 | B2 | 4/2011 | Beeman |
| 2013/0224771 | A1 | 8/2013 | McDade |

OTHER PUBLICATIONS

Anonymous, CHMlab. Ashless Hardened Filter Paper for Quantitative Analysis; downloaded from http://www.chmlab.com/en/Filtration/Quantitative-Filter-Paper/Ashless-hardened-fliter-paper-for-quantitative-analysis/ (Year: 2005).
Anonymous, What is Deionized Water?, downloaded from https://puretecwater.com/deionized-water/what-is-deionized-water (Year: 2012).
Anonymous. Advantec Specialty Products, pp. 31-46. Downloaded from https://web.archive.org/web/20091116173315/http://www.advantecmfs.com/catalog/filt/specialty.pdf on Oct. 29, 2018 (Year: 2009).
Anonymous. Taking Blood From Infants for the HIV PCR Test; (2011) downloaded from http://www.nhls.ac.za/assets/files/3458%20Roche%20DBS%20Booklet%20LR.pdf on Jun. 13, 2017.
Anonymous. The Seven Strong Acids, downloaded from https://web.archive.org/web/20031027165745/http://www.cm.utexas.edu/academic/courses/Spring2002/CH301/McDevitt/strong.htm (Year: 2003).
Anonymous. Whatman: Touching Lives; Product Guide 2010-2011, downloaded from Http://www.laboplus.pl/images/stories/katalogi/2010_whatman_catalog_full_fnl.pdf on Sep. 18, 2017.
Barbee JY Jr, et al (1999) Acute respiratory dislress syndrome in a welder exposed to metal fumes. South Med J 92: 510-512.
Bean HD, et al (2015) Editorial: new analytical and statistical approaches for interpreting the relationships among environmental stressors and biomarkers. Biomarkers 20: 1-4.
Behbahani M, et al. (2014) Monitoring of trace amounts of heavy metals in different food and water samples by flame atomic absorption spectrophotometer after preconcenlalion by amine-functionalized graphene nano sheet. Environ Monit Assess 186: 7245-7257.
Canadian Health Measures Survey 2015.
Chaudhuri, SN., et al. "Pilot study for utilization of dried blood spots for screening of lead, mercury and cadmium in newborns." Journal of Exposure Science and Environmental Epidemiology 19.3 (2009): 298.
Davit CJ, et al (2011) A pilot study to improve venipuncture compliance in children and adolescents with autism spectrum disorders. J Dev Behav Pediatr 32: 521-525.
Demetriou CA, et al (2015) Carcinogenicity of ambient air pollution: use of biomarkers, lessons learnt and future directions. J Thorac Dis 7: 67-95.
Fisher Chemical. High Purity Acids Trace Elemental Analysis; downloaded from https://acros.com/myBrochure/FC_High_Purity_Acids_EEM.pdf on Oct. 29, 2018 (Year: 2012).
Funk WE, et al (2013) Quantification of arsenic, lead, mercury and cadmium in newborn dried blood spots. Biomarkers 18: 174- 177.
Funk WE, et al (2008) Hemoglobin adducts of benzene oxide in neonatal and adult dried blood spots. Cancer Epidemiol Biomarkers Prev 17: 1896-1901.
Guthrie R, et al (1963) A simple phenylalanine method for detecting phenylketonuria in large populations of newborn infants. Pediatrics 32: 338-343.
Harper M, et al. (2015) Commentary on the contributions and future role of occupational exposure science in a vision and strategy for the discipline of exposure science. Journal of exposure science and environmental epidemiology 25: 381-387.
International Preliminary Report on Patentability for PCT/US2014/028146 dated Oct. 1, 2015.
International Preliminary Report on Patentability for PCT/US2014/028146 dated Sep. 22, 2015.
International Search Report for PCT/US2014/028146 dated Jul. 29, 2014.
Jarup L (2003) Hazards of heavy metal contamination. Br Med Bull. 68:167-182.
Laan. Area and Volume of Blood Drops: Using Optical Coherence Tomography to Determine the Volume of Bloodstains. Masters Thesis. Jan. 10, 2011.
Langer, E. K., et al. "Characterization of the elemental composition of newborn blood spots using sector-field inductively coupled plasma-mass spectrometry." Journal of Exposure Science and Environmental Epidemiology vol. 21, No. 4, pp. 1-21 (Year: 2011).
Lee et al. Estimation of Metal Impurities in High-Purity Nitric Acids Used for Metal Analysis by Inductively Coupled Plasma-Mass Spectrometry; Analytical Sciences, vol. 19, pp. 1561-1563. (Year: 2003).
Matoug, I. O. M. "Study of metals contamination in different filter papers." J. Environ. Sci. Toxicol. Food Technol. (IOSR-JESTFT) 3 (2013): 59-61.
McDade TW, et al. (2007) What a drop can do: dried blood spots as a minimally invasive method for integrating biomarkers into population-based research. Demography 44: 899-925.
Mei, J.V., et al. "Use of filter paper for the collection and analysis of human whole blood specimens." The Journal of nutrition 131.5 (2001): 1631S-1636S.
Miller MG (2007) Environmental metabolomics: A SWOT analysis (strengths, weaknesses, opportunities, and threats). J Proteome Res 6: 540-545.
Olshan AF (2007) Meeting report: the use of newborn blood spots in environmental research: opportunities and challenges. Environ Health Perspect 115: 1767-1779.
Park HA (2013) The Korea national health and nutrition examination survey as a primary data source. Korean J Fam Med 34: 79.
Pigatto PD, et al. (2013) Human placenta and markers of heavy metals exposure. Environ Health Perspect 121:A10.
Pleil JD (2012) Categorizing biomarkers of the human exposome and developing metrics for assessing environmental sustainability. J Toxicol Environ Health B Crit Rev 15: 264-280.
Pleil JD, et al. (2012) Establishing exposure science as a distinct scientific discipline. J Expo Sci Environ Epidemiol 22: 317-319.
Pleil JD, et al. (2011) Adapting concepts from systems biology to develop systems exposure event networks for exposure science research. Biomarkers 16: 99-105.
Pleil JD, et al. (2014) Estimating common parameters of log normally distributed environmental and biomonitoring data: harmonizing disparate statistics from publications. J Toxicol Environ Health B, Crit Rev 17: 341-368.
Rappaport SM, et al. (2010) Epidemiology. Environment and disease risks. Science 330: 460-461.
Roels H, et al. (1978) Placental-transfer of lead, mercury, cadmium, and carbon-monoxide in women III. Factors influencing accumu-

(56) References Cited

OTHER PUBLICATIONS lation of heavy-metals in placenta and relationship between metal concentration in placenta and in maternal and cord blood. Environ Res. 16: 236-247.

Roychowdhury, T et al (2003) Survey of arsenic and other heavy metals in food composites and drinking water and estimation of dietary intake by the villagers from an arsenic-affected area of West Bengal, India. The Science of the Total Environment 308: 15-35.

Scribner et al. Development of Standards for Analytical Papers; U.S. Department of Commerce, National Bureau of Standards, Research Paper RP1809, vol. 39, pp. 21027.

Seidal K, et al. (1993) Fatal cadmium-induced pneumonitis. Scand J Work Environ Health 19: 429-431.

Sobus JR, et al. (2015) Uses of NHANES biomarker data for chemical risk assessment: Trends, challenges, and opportunities. Environmental Health Perspectives.

Sobus JR, et al. (2011) A biomonitoring framework to support exposure and risk assessments. Sci Total Environ 409: 4875-4884.

Sorensen M, et al. (2003) Linking exposure to environmental pollutants with biological effects. Mutat Res 544: 255-271.

Stove et al. Dried Blood Spots in Toxicology: From the Cradle to the Grave; Critical Reviews in Toxicology, vol. 42, No. 3 pp. 23-243. (Year: 2012).

Tan YM, et al. (2012) Reconstructing human exposures using biomarkers and other "clues". J Toxicol Environ Health B Crit Rev 15: 22-38.

Wild CP (2005) Complementing the genome with an "exposome": the outstanding challenge of environmental exposure measurement in molecular epidemiology. Cancer epidemiology, biomarkers and prevention 14: 1847-1850.

Written Opinion for PCT/US2014/028146 dated Jul. 29, 2014.

Zheng J, et al. (2013) Heavy metals in food, house dust, and water from an e-waste recycling area in South China and the potential risk to human health. Ecotoxicol Environ Saf 96: 205-212.

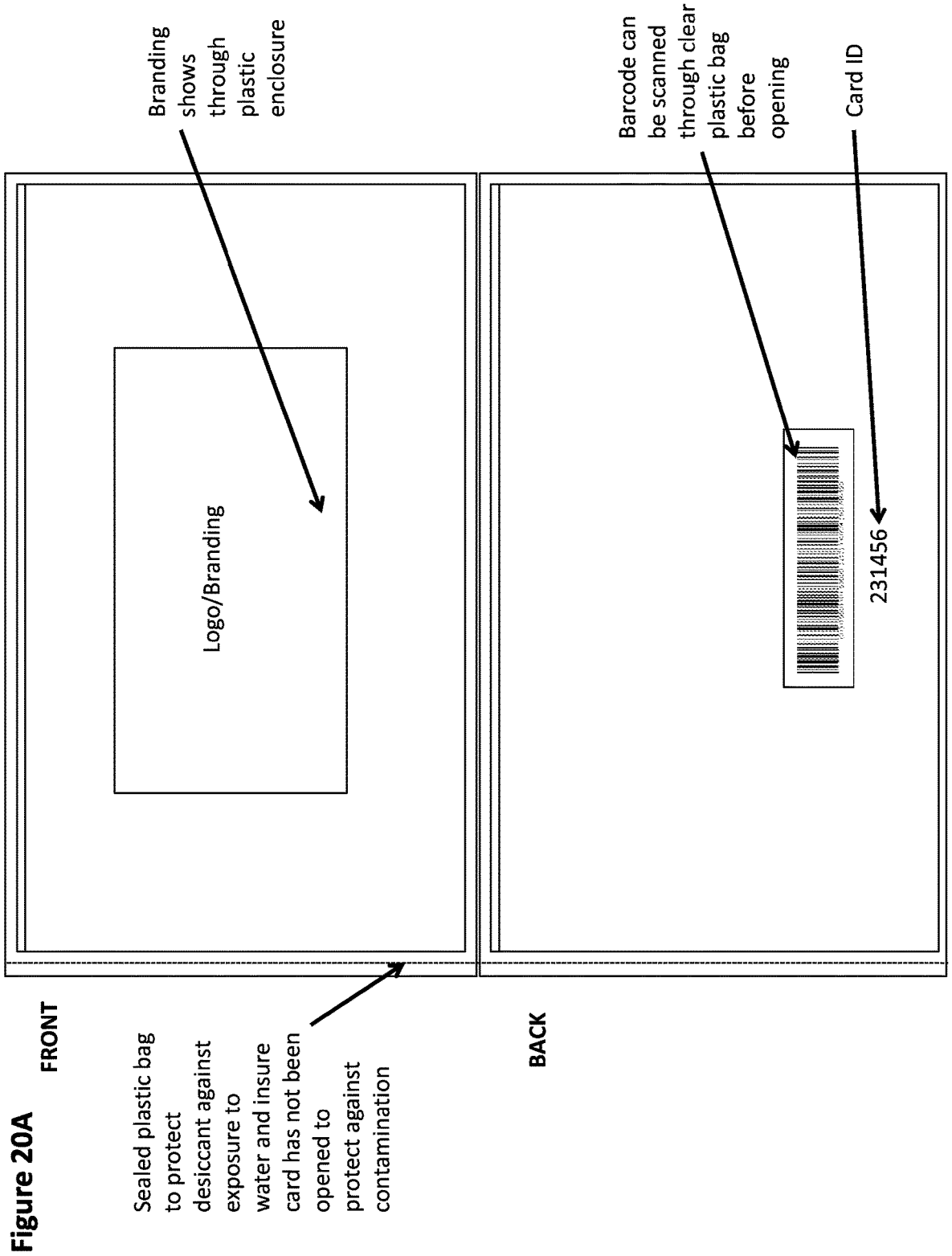

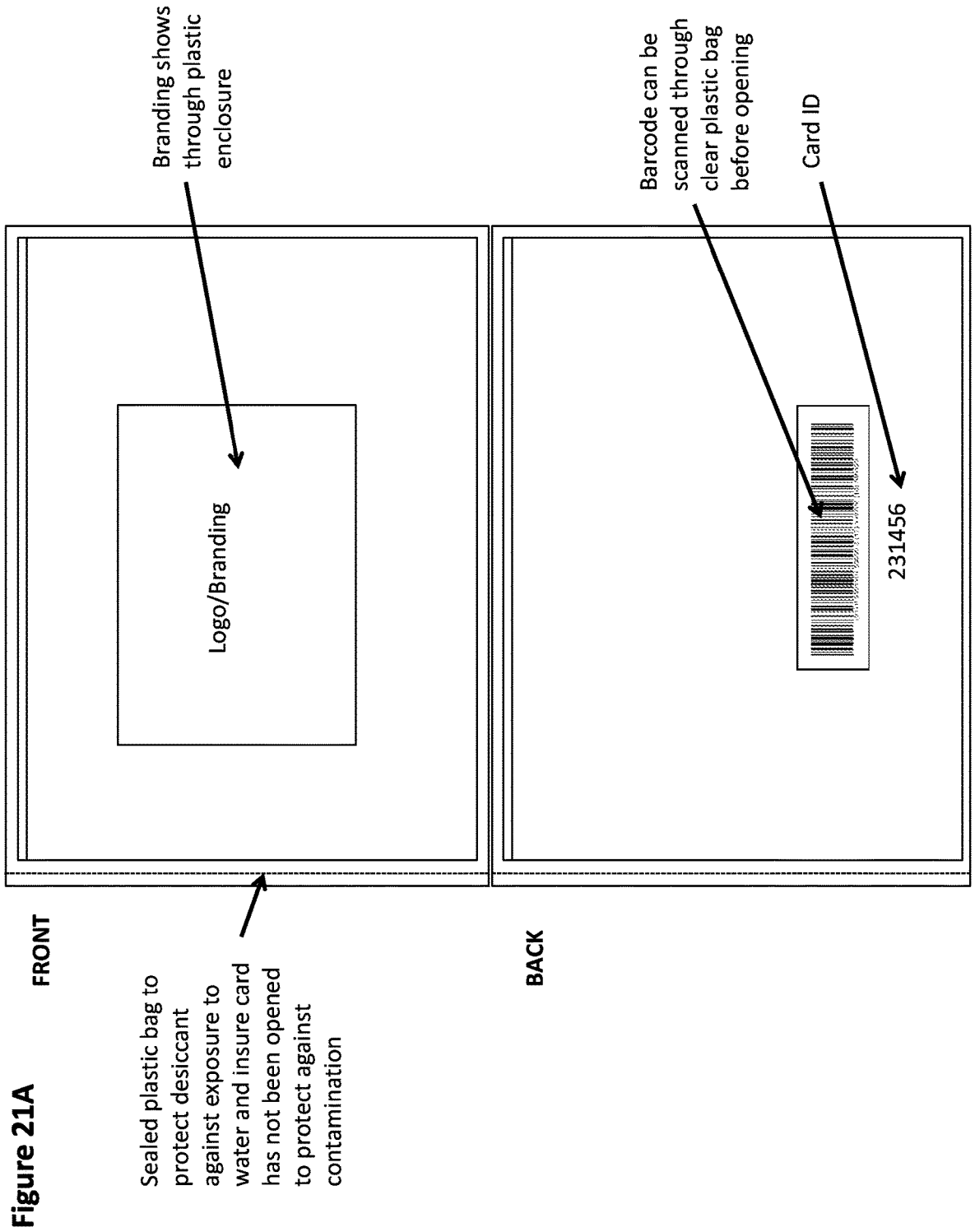

METHODS FOR COLLECTING BIOLOGICAL SAMPLES FOR QUANTIFYING HEAVY METALS

CROSS-REFERENCE TO RELATED PATENT APPLICATIONS

The present application is a continuation of U.S. patent application Ser. No. 15/602,864, filed May 23, 2017, which is a continuation-in-part of U.S. patent application Ser. No. 14/778,234, filed on Sep. 18, 2015, which is the U.S. national stage of International Application PCT/US2014/028146, filed on Mar. 14, 2014, which claims the benefit of priority to U.S. Provisional Application No. 61/803,674, filed on Mar. 20, 2013, the contents of which applications are incorporated herein by reference in their entireties. The present application claims the benefit of prior to U.S. Provisional Application No. 62/340,261, filed on Mar. 23, 2016, the content of which is incorporated herein by reference in its entirety.

STATEMENT REGARDING FEDERALLY SPONSORED RESEARCH OR DEVELOPMENT

This invention was made with government support under HHSN267200700027C awarded by the National Institutes of Health. The government has certain rights in the invention.

BACKGROUND

The invention relates to systems, devices, kits, compositions, and methods for detecting toxicants, pathogens, and biomarkers in a biological sample. The systems, devices, kits, compositions, and methods may be utilized safely to collect, process, and transport biological samples, such as a dried blood sample from a skin prick, to a reference laboratory.

Toxicants, such as heavy metals including arsenic (As), lead (Pb), mercury (Hg), and cadmium (Cd), are ubiquitous environmental toxicants. In fact, As, Pb, Hg, and Cd are listed as the $1^{st}$, $2^{nd}$, $3^{rd}$, and $7^{th}$ most important hazardous substances on the 2011 CERCLA priority list of 275 substances, respectively. Exposure to heavy metals can occur through a variety of exposure routes, including inhalation as dust and fumes, and ingestion from food and water, and can cause a wide spectrum of health problems including convulsions, coma, renal failure, injuries to the lungs and neurologic system, memory loss, delirium, diabetes, kidney damage, and a variety of cancers.

Currently the "gold standard" for quantifying heavy metals in blood is to use whole blood collected by venipuncture. Because venous blood collection is costly, invasive, and must be performed by a trained phlebotomist, these obstacles constrain screening efforts for assessing exposure to toxic metals in non-clinical settings. In addition, heavy metals such as lead are routinely measured in clinical settings in younger children, often as part of state mandated screening programs to assess environmental exposures. Younger children are more difficult to phlebotomize Given the draw backs of venipuncture based methods, a dried blood sample approach using simple and minimally invasive methods (e.g., based on a finger prick or heel prick) has large advantages for both population based surveys, public health surveillance, and standard clinical testing.

Newborn Screening (NS) for detection of inherited or prenatally acquired diseases is a routine aspect of newborn care in all developed nations. NS utilizes unsealed, air-dried filter paper dried blood spot (DBS) paper "cards" that contain sensitive personal and private information as to the patient and his/her parents, as well as blood specimens, usually obtained by heelstick, for laboratory analysis.

The most common filter paper used to collect newborn DBS samples is Whatman #903 Protein Saver Cards. However, while Whatman #903 filter paper and filter paper in general have been rigorously tested and optimized for measuring a variety of biomarkers, they are not designed for collecting blood samples and performing trace level heavy metals analysis. This is at least partially because background contamination in the filter paper (e.g., at ppb) interferes with quantification of heavy metals in DBS samples and can lead to imprecise estimates of exposure.

An additional challenge for quantifying biomarkers in DBS samples is the unknown volume of blood in each sample. DBS are generally collected via a simple finger or heel prick, and as a result, the volume of blood applied to the filter paper is unknown. The common convention for determining blood volume is to take a standard punch from the blood spot (typically 3-6 mm in diameter) and estimating the blood volume based on the size of the punch. However, these crude approximations result in too much measurement error for the precise quantification of heavy metals, which are present in very small quantities (e.g., at ppb).

In addition to toxicants, infectious diseases are a leading cause of death, disability, suffering, and medical expense among newborns and children worldwide. Epidemics of novel, often potentially fatal, illnesses such as MERS, Avian Flu, Ebola, Zika are being recognized with ever-greater frequency worldwide as population mobility and density increases globally. The potential for genetic manipulation of known pathogens to increase both transmissibility and virulence remains a national security threat. Blood (or other biological specimens) spotted onto filter paper cards cannot presently safely be used for analysis of novel potential infection(s) because of uncertainty as to transmission potential, should such cards be allowed to simply air dry and then be shipped by standard ground carrier to reference labs—as is the current situation with Government-sponsored NS programs. In particular, the current DBS NS card is not compatible with the collection of urine for subsequent laboratory analysis. This is a critical current deficit as urine Zika viral loads as quantified by RT PCR are more persistent, and provide better diagnostic information, than blood Zika viral levels. Zika viruria is detectable at low fluid volume.

Here, we disclose systems, devices, kits, compositions, and methods to overcome these problems in the art. The disclosed systems, devices, kits, compositions, and methods may be used safely to collect, transport, and test a biological sample, such as a dried blood sample from a skin prick, for toxicants, such as heavy metals and other toxicants. In addition, the disclosed systems, devices, kits, compositions, and methods may be used safely to collect, transport, and test a biological sample, such as a dried blood sample from a skin prick for pathogens, such as bacterial and viral pathogens, and for biomarkers.

SUMMARY

Disclosed are systems, devices, kits, compositions, and methods for collecting, transporting, and detecting toxicants, pathogens, and biomarkers in a biological sample. In particular, the systems, devices, kits, compositions and methods may be utilized to collect and transport biological samples, such blood samples from a skin prick, urine, and other biological specimens, and detect in the biological samples toxicants, such as heavy metals, pathogens, such as bacteria and virus, and biomarkers.

The devices disclosed herein for collecting blood samples and detecting toxicants, pathogens, and biomarkers in dried blood spots may include one or more of the following components: (a) a support card, which preferably is folded or foldable; (b) a treated sample pad that is free of detectable levels of contaminants, such as heavy metals, and optionally where the treated sample pad is adhered to the support card on a section of the support card that is free of detectable levels of contaminants; (c) a desiccant, which optionally may be adhered to the support card, and; (d) an adhesive that is configured for sealing the sample pad and the desiccant in the support card when the support card is folded to encase the sample pad and desiccant inside the folded support card. Preferably, the devices disclosed herein are enclosed in a sealed and resealable container which may be opened in order to apply a blood sample to the device (e.g., at the treated sample pad), and after which may be resealed to prevent contamination of the blood sample thus applied.

The treated sample pad present in the disclosed device may be formed from any suitable material. In some embodiments, the treated sample pad may comprise, consist essentially of, or consist of cellulose (e.g., filter paper and in particular Whatman™ 903 brand specimen collection paper), which optionally may be perforated to facilitate removal of the sample pad from the support card after a blood sample has been applied to the treated sample pad and prior to extracting the blood sample from the treated sample pad and assaying the extracted blood sample for toxicants, pathogens, and biomarkers.

The treated sample pad utilized in the disclosed methods typically is free of detectable levels of contaminants, such as heavy metals, other toxicants, pathogens, and/or biomarkers. In this regard, when the sample pad is extracted with ~1 ml of an extraction solution for detecting heavy metals, the extraction solution should comprise no more than about 5, 4, 3, 2, 1, 0.5, or 0.1 ppb of a heavy metal. Preferably, a treated sample pad having a diameter of approximately ½ inch comprises no more than about 5, 4, 3, 2, 1, 0.5, or 0.1 ng of a heavy metal. The treated sample pad typically will hold a volume blood sample of about 50, 60, 70, 80, 90, 100 µl or a range bounded by any two of these values (e.g., 50-100 µl of a blood sample).

The treated sample pad may be prepared by treating an untreated sample pad with an acid that is free of detectable levels of toxicants such as heavy metals, which optionally may be an inorganic acid. Suitable acids may include but are not limited to nitric acid, hydrochloric acid, or a mixture thereof. In some embodiments, the acid is diluted in ultra-pure water which optionally is deionized water to a concentration value of less than about 10%, 9%, 8%, 7%, 6%, 5%, 4%, 3%, 2%, or 1% acid, or to a concentration range of acid bounded by any two of these concentration values.

The devices may include additional sample pads further to the treated sample pad. The additional sample pads may be treated or untreated and be utilized for collecting additional blood samples for screening for other toxicants (e.g., environmental toxicants such as perfluorooctane sulfonate (PFOS), perfluorooctanoate (PFOA), polychlorinated biphenyls (PCBs), and the like) and for collecting additional blood samples for screening for pathogens (e.g., bacterial and/or viral pathogens) and/or biomarkers. As such, the disclosed devices may be utilized in multiplex systems for detecting toxicants (e.g., such as heavy metals and other toxicants), pathogens (e.g., bacterial, viruses, and other toxicants), and biomarkers (e.g., DNA biomarkers indicative of paternity, genetic abnormalities, and the like, or protein biomarkers such as C-reactive protein and inflammatory cytokines).

The sample pads of the device may be pre-treated (or doped) with reagents that are useful for detecting toxicants, pathogens, and biomarkers. In some embodiments, the sample pads may be pre-treated with nucleic acid reagents that are useful for detecting pathogens and biomarkers (e.g., nucleic acid reagents that are used as primers and/or probes, which may allow rapid, inexpensive, on-site diagnosis of infection by lateral diffusion immunochromatography).

The support card of the disclosed devices further may comprise a tag, such as a readable bar code. The tag may be used for identifying and/or tracking a blood sample applied to the sample pad. The disclosed devices each may have its own Unique Personal Identification Number (UPIN) expressed as a bar code that may be scanned through a transparent plastic bag, and then linked electronically to a UPIN for a NS card. The support card of the disclosed devices may be attached and detachable from a NS card, where a bar code providing a UPIN is printed across the detachment site such that it is shared physically by both the NS card and the support card, and split physically with retained readability when the support card is detached, thus maintaining a single UPIN for both of the NS card and the support card of the device.

The support card of the device may be folded or foldable. When unfolded, the support card comprises a front and a back. The treated sample pad and desiccant may be adhered to the front of the support card, and the tag may be adhered to the back of the support card. As such, when the support card is folded the front including the treated sample pad and desiccant adhered thereto are encased on the inside of the folded support card, and the back including the tag adhered thereto are located on the outside of the folded support card.

The devices or any of the components thereof preferable are contained in a sealed and resealable container, such as a sealed bag or sleeve, which may be opened and resealable after a biological sample is applied to one or more sample pads of the device. In some embodiments of the sealed container, the sealed container is a sealed bag or sealed sleeve which is perforated at an end to facilitate opening of the sealed bag or sealed sleeve and removal of the device contained in the sealed bag by opening the sealed bag or sealed sleeve at the perforated end. The combination of the device for collecting blood samples contained in the sealed and resealable container may be referred to as a "system" for collecting blood samples. The sealed container typically is free of detectable levels of contaminants such as heavy metals and pathogens. The sealed container may include an adhesive on the outside of the sealed container for adhering the sealed container to a master support card such as a standard newborn screening card, optionally wherein the master support card comprise a tag that may correlated to the tag of the device contained in the sealed container. As such, the devices may be integrated into existing devices for screening for toxicants, pathogens, and biomarkers. The adhesive may be present as an adhesive strip that is covered by a removable paper cover.

The methods disclosed herein may include methods of detecting a toxicant such as a heavy metal in a subject and/or determining the approximate venous concentration of a toxicant such as a heavy metal in a subject. Optionally, the methods may utilize the presently disclosed devices for collecting blood samples and detecting heavy metals in dried blood spots. The disclosed methods may include one or more of the following steps: a) applying a whole blood sample from a skin prick of the subject to a treated sample pad that is free of detectable levels of heavy metals (e.g., a treated sample pad of the devices disclosed herein); b) extracting the whole blood sample from the treated sample pad into an extraction solution; c) determining the approximate concentration of the heavy metal in the extraction solution; and d) determining the approximate venous concentration of the heavy metal based on the determined approximate concentration of the heavy metal in the extraction solution. The heavy metals detecting in the disclosed methods may include one or more of As, Pb, Hg, and Cd, and/or other elemental compounds.

The extraction solution used in the disclosed methods typically is free of detectable levels of contaminants such as heavy metals. Preferably, the extraction solution comprises heavy metals at a concentration of less than about 5, 4, 3, 2, 1, 0.5, or 0.1 ppb.

The extraction solution may comprise an acid, and optionally may comprise a short chain carboxylic acid, which is free of detectable levels of contaminants such as heavy metals. Suitable acids may include acetic acid or any $C_1$-$C_6$ carboxylic acid, which may include branched or straight chain carboxylic acids. The acid may be present at any suitable concentration including concentration values of 1%, 2%, 3%, 4%, 5%, 6%, 7%, 8%, 9%, 10%, 15%, 20%, or within a suitable concentration range bounded by any two of these values.

Optionally, the extraction solution may comprise a detectable agent as a control. The detectable agent may comprise a metal, such as indium, bismuth, yittrium, and/or other rare elements. Optionally, the extraction solution may comprise an amalgam agent that binds Hg (e.g., gold) to prevent analyte loss during sample extraction and analysis.

The extraction solution may comprise a surfactant, and optionally a non-ionic surfactant, which is free of detectable levels of contaminants such as heavy metals. Suitable surfactants may include Triton X-100. The surfactant may be present at any suitable concentration including concentration values of 0.005%, 0.01%, 0.02%, 0.05%, 0.1%, 0.2%, 0.5%, 1.0%, 2.0%, or within a suitable concentration range bounded by any two of these values.

The extraction solution typically is an aqueous solution comprising ultrapure water. Optionally, the ultrapure water is deionized water.

In the disclosed methods, the approximate concentration of the heavy metal in the extraction solution may be determined using any suitable means. In some embodiments, the approximate concentration of the heavy metal in the extraction solution may be determined using mass spectrometry.

In the disclosed methods, the approximate venous concentration of the heavy metal typically is determined based on the determined approximate concentration of the heavy metal in the extraction solution. For example, the determined approximate concentration of the heavy metal in the extraction solution may be multiplied by a conversion factor in order to determine the approximate venous concentration of the heavy metal. (See, e.g., conversion factors described in Funk et al., "Use of Dried Blood Spots for Estimating Children's Exposures to Heavy Metals in Epidemiological Research," *J. Environ. & Analyt. Toxicology* 2015, S7, ISSN: 2161-0525, published on Jul. 24, 2015, a copy of which is enclosed as Appendix II to this application and is incorporated herein by reference in its entirety.

The disclosed methods further may include methods of detecting other toxicants such as PFOS, PFOA, PCBs in a subject and/or determining the approximate venous concentration of other toxicants in a subject. The methods further may include methods of detecting a pathogen and/or determining the approximate venous concentration of a pathogen in a subject. The methods further may include methods of detecting a biomarker in a subject such as DNA biomarkers and/or protein biomarkers including biomarkers associated with inflammation, oxidative stress, nutritional status, and health.

Also disclosed herein are methods for making a treated sample pad, which optionally may be used in the methods disclosed herein or present in the devices or kits disclosed herein. The methods for making the treated sample pad may include treating an untreated sample pad, which optionally comprises detectable levels of contaminants such as heavy metals, with an acid under conditions such that the treated sample pad is free of detectable levels of contaminants such as heavy metals. The methods may include submerging the untreated sample pad into the acid, optionally agitating untreated sample pad as it is submerged the acid, and rinsing the sample pad with deionized water to remove the acid. Suitable acids for preparing the treated sample pad include, but are not limited to inorganic acids that are free of detectable levels of contaminants such as heavy metals (e.g., nitric acid, hydrochloric acid, or a mixture thereof, which optionally may be diluted with ultrapure water to a suitable concentration value as described herein). After treatment, a treated sample pad having a diameter of approximately ½ inch comprises no more than about 5, 4, 3, 2, 1, 0.5, or 0.1 ng of a heavy metal.

Also disclosed are kits for detecting toxicants, pathogens, and biomarkers in dried blood. The kits optionally may be used in the methods disclosed herein and optionally may include the devices or components thereof as disclosed herein. In some embodiments, the kit comprises: a) a first component comprising a sample pad that is free of detectable levels of contaminants such as heavy metals and pathogens; and b) one or more second components selected from the group consisting of: i) a skin cleansing wipe this is free of detectable levels of contaminants; ii) a support card to which the sample pad is adhered, wherein the sample pad is adhered to a section of the support card that is free of detectable levels of contaminants; iii) a desiccant optionally adhered to the support card of second component ii); iv) a lancing device configured to pierce human skin, wherein the lancing device is free of detectable levels of contaminants; v) an extraction solution for extracting a blood sample from the sample pad, wherein the extraction solution is free of detectable levels of contaminants; and vi) a sealed bag comprising the first component and one or more of the second components i)-vii). Optionally, the kits include one or more additional sample pads that are treated or untreated for collecting a biological sample and detecting additional toxicants, pathogens, and/or biomarkers.

BRIEF DESCRIPTION OF THE FIGURES

FIGS. 20A, and 20B illustrate one embodiment collection systems and device as contemplated herein.

FIGS. 21A, and 21B illustrate one embodiment collection systems and device as contemplated herein.

DETAILED DESCRIPTION

Figure 1:
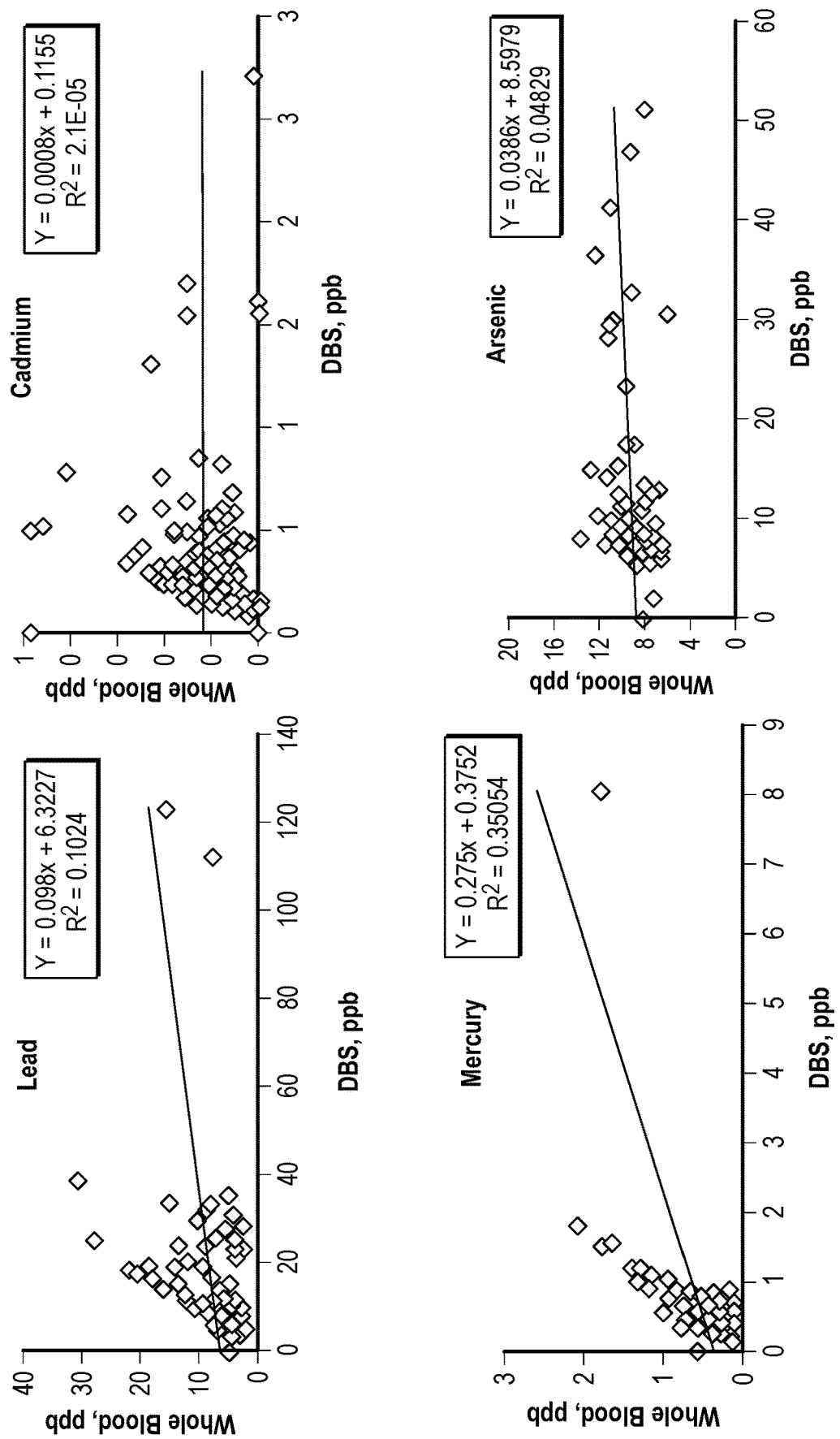
FIG. 1 shows a scatterplot and regression analysis from Example 1 below of the association between heavy metal concentrations obtained from matched venous whole blood and finger stick DBS samples for n=85 children.

The present invention is described herein using several definitions, as set forth below and throughout the application.

Definitions

Unless otherwise specified or indicated by context, the terms "a", "an", and "the" mean "one or more." For example, "a sample pad" should be interpreted to mean "one or more sample pads."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "patient" may be interchangeable with "subject" or "individual" and means an animal, which may be a human or non-human animal, in need of treatment or diagnosis. A "patient in need of treatment or diagnosis" may include a patient exposed to toxicants such as heavy metals or at risk for exposure to toxicants such as heavy metals. A "patient in need of treatment or diagnosis" may include a patient exposed to pathogens or at risk for exposure to pathogens. A "patient in need of treatment or diagnosis" may include a patient having a biomarker such as a DNA biomarker indicative of paternity, a genetic abnormality, or the like or a protein biomarker indicative of disease such as C-reactive protein and/or inflammatory cytokines.

As used herein, a "biological sample" may include, but is not limited to biological fluids such as blood or blood products (e.g., whole blood, serum, or plasma), urine, saliva, breast milk and the like. A biological sample may include a dried blood sample.

The biological samples utilized herein may include blood samples obtained from a "skin prick" which alternatively may be referred to as a "skin stick." A "skin stick" refers to a method whereby a patient's skin is penetrated with a needle-like instrument or lance which causes the patient to bleed typically a drop-size volume of whole blood (i.e., about 10, 20, 30, 40, 50, 60, 70, 80, 90, 100 µl or a volume range bounded by any two of these values).

As used herein, the term "contaminant" means any matter that interferes with detecting an "analyte" in an assay of a biological sample. "Analytes" may include but are not limited to toxicants, pathogens, and biomarkers. As such, contaminants may include, but are not limited to toxicants and/or pathogens present on untreated sample pads. Toxicants may include, but are not limited to heavy metals (e.g., As, Pb, Hg, and Cd), mercury (Hg), petroleum products, and polychlorinated biphenyls (PCB). Pathogens may include but are not limited to bacteria, viruses (e.g., Zika virus), fungi, and other microbial agents. Biomarkers may include DNA markers indicative of paternity, genetic abnormality or disease, or the like and/or protein markers indicative of disease.

Disclosed are devices, kits, compositions and methods for collecting blood samples and detecting toxicants, such as heavy metals, detecting pathogens, and/or detecting biomarkers in blood samples including dried blood samples (e.g., dried blood samples obtained from skin pricks, such as finger or heel pricks). For example, disclosed are devices, kits, compositions and methods that include or utilize: 1) one or more sample pads that are detectably free of contaminants such as heavy metals and pathogens and methods of preparing such a sample pad using acid; 2) extraction solutions, optionally optimized for toxicants such as heavy metals (e.g., extraction solutions containing acetic acid, an ionic surfactant, and/or an internal heavy metal standard such as indium, bismuth, yttrium, and/or other rare elements); 3) methods for estimating venous blood volume from dried blood mass; and 4) components optimized for detecting toxicants such as heavy metals in dried blood (e.g., contaminant-free skin wipes, a contaminant-free collection device with contaminant-free components, and the like) and optionally components for detecting pathogens and/or biomarkers.

The disclosed methods, compositions, kits, and devices may be utilized for detecting heavy metals in dried blood (e.g., dried blood spots). In some embodiments, the disclosed subject matter relates to: 1) dried blood spot paper that is detectably free of heavy metals and methods of preparing such paper using organic acid; 2) dried blood extraction solutions optimized for heavy metal detection (e.g., extraction solutions containing acetic acid and/or gold); 3) methods for estimating venous blood volume from dried blood mass; and 4) kits and kit components optimized for heavy metal detection in dried blood (e.g., kits with paper detectably free of heavy metals, heavy metal free skin wipes, metal free collection case, etc.).

Environmental exposures to heavy metals are a large concern globally, and have been a focus of many population based surveys. Currently the "gold standard" for quantifying heavy metals in blood is to use whole blood collected by venipuncture. Because venous blood collection is costly, invasive, and must be performed by a trained phlebotomist, these obstacles have been a challenge for assessing exposure to toxic metals in non-clinical settings. In addition, heavy metals (e.g. Pb) are routinely measured in clinical settings, often as part of state mandated screening programs, in younger children to assess environmental exposures. Given the draw backs of venipuncture based methods, the dried blood sample approach of the present invention provides a simple and minimally invasive methods (e.g., based on finger prick) that has large advantages for both population based surveys, public health surveillance, and standard clinical testing.

The most common filter paper used to collect dried blood spot (DBS) samples is Whatman #903 Protein Saver Cards. However, while Whatman #903 filter paper has been rigorously tested and optimized for measuring a variety of biomarkers, they are not designed for trace level heavy metals analysis. As a result, background contamination in the filter paper interferes with quantification of heavy metals in DBS samples and can lead to imprecise estimates of exposure.

An additional challenge for quantifying biomarkers in DBS samples is the unknown volume of blood in each sample. DBS are generally collected via a simple finger or heel stick, and as a result, the volume of blood applied to the filter paper is unknown. The common convention for determining blood volume is to take a standard punch from the blood spot (typically 3-6 mm in diameter) and estimating the blood volume based on the size of the punch. However, these crude approximations result in too much measurement error for the precise quantification of heavy metals, which are present in very small quantities.

The disclosed methods, devices, kits, and compositions overcome the problems in the art. In certain embodiments, the disclosed subject matter relates to DBS specimen collection devices that are optimized for quantification of trace level heavy metals. Examples of the innovations provided herein may include the following: 1) methods for pretreating the filter paper matrix to remove heavy metal contamination prior to blood collection; 2) an algorithm for determining blood volume, based on the mass of the blood collection device before and after blood collection; 3) a blood collection device in which the pretreated filter paper is secured to a metal-free plastic (e.g., polypropylene) ring to protect the blood collection surface from contacting surfaces that may contaminate the blood sample; 4) a blood collection device that is contained inside a metal-free plastic (e.g., polypropylene) case to avoid contamination before, during, and after blood collection; 5) the use of a desiccant in the plastic case, preferably positioned beneath a metal-free plastic grid, to absorb water as the sample is dried within the protective encasement; 6) use of a metal-free alcohol wipe pad for cleaning the skin (e.g., finger) prior to blood collection, to eliminate contamination from the finger (and to reduce risk of infection at the site of puncture); and 7) points 4 and 6 above facilitating the shipment of samples without concerns about stability or contamination, and allow for the collection of samples in home, community, and clinic based settings (which is not the case with venipuncture-based collection methods).

Figure 7:
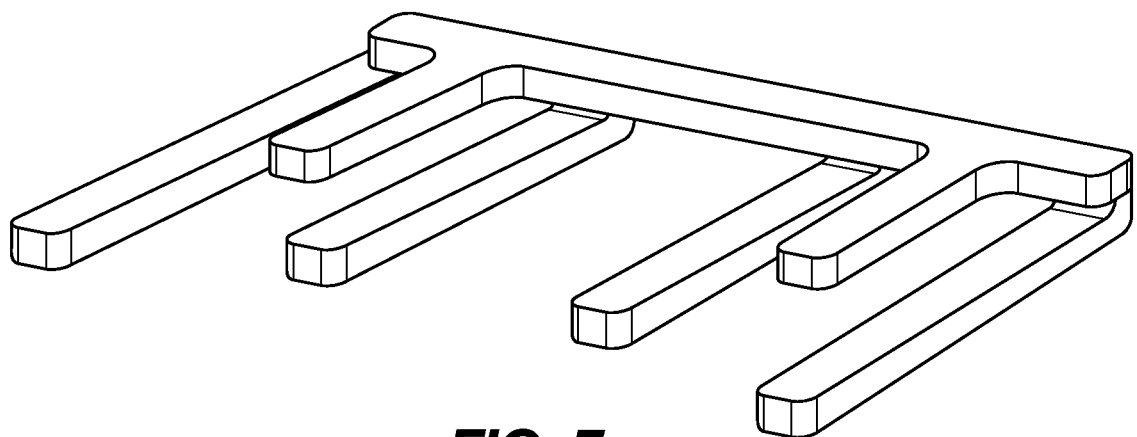
FIG. 7 shows an exemplary plastic support configured to hold filter paper (e.g., and to provide a spacer between the paper and desiccant inside the collection case). The exemplary plastic support in FIG. 7 has two upper prongs and four lower prongs attached to a base rod and is free of detectable levels of heavy metals. In certain embodiments, different numbers of upper and lower prongs are employed (e.g., three-six lower prongs and five-eight upper prongs, etc.).
Figure 8:
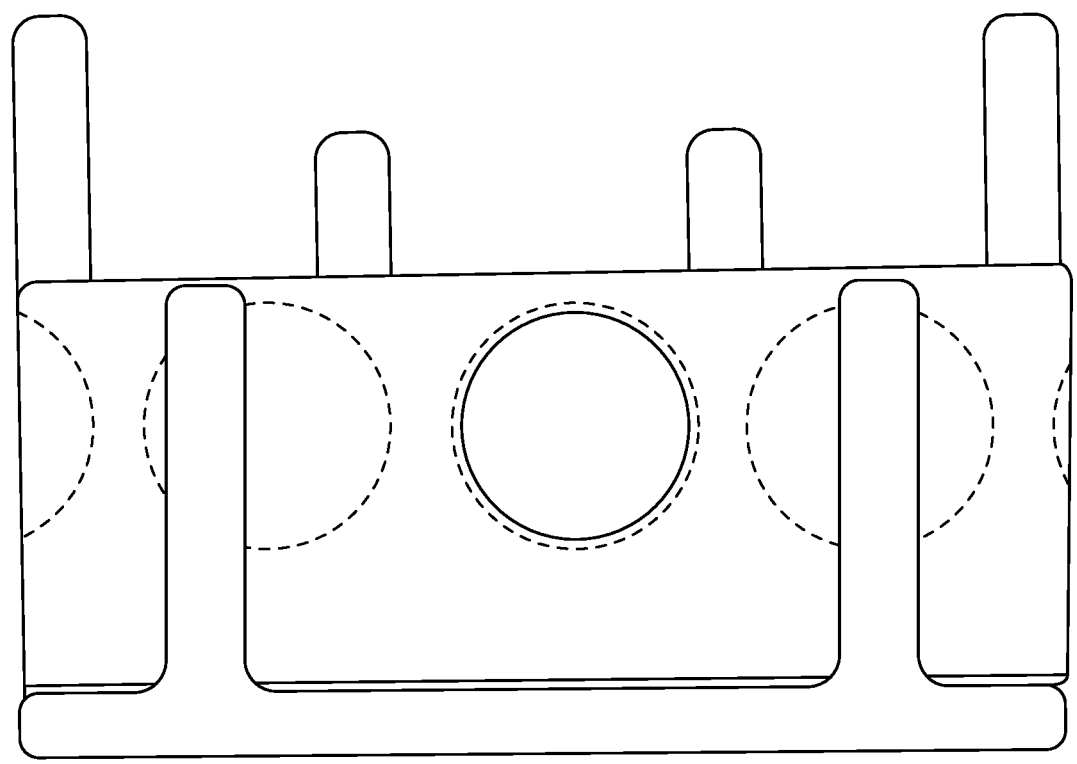
FIG. 8 shows the same type of exemplary plastic support as in FIG. 7, but includes filter paper inserted therein, wherein the filter paper contains a dried blood spot.
Figure 9:
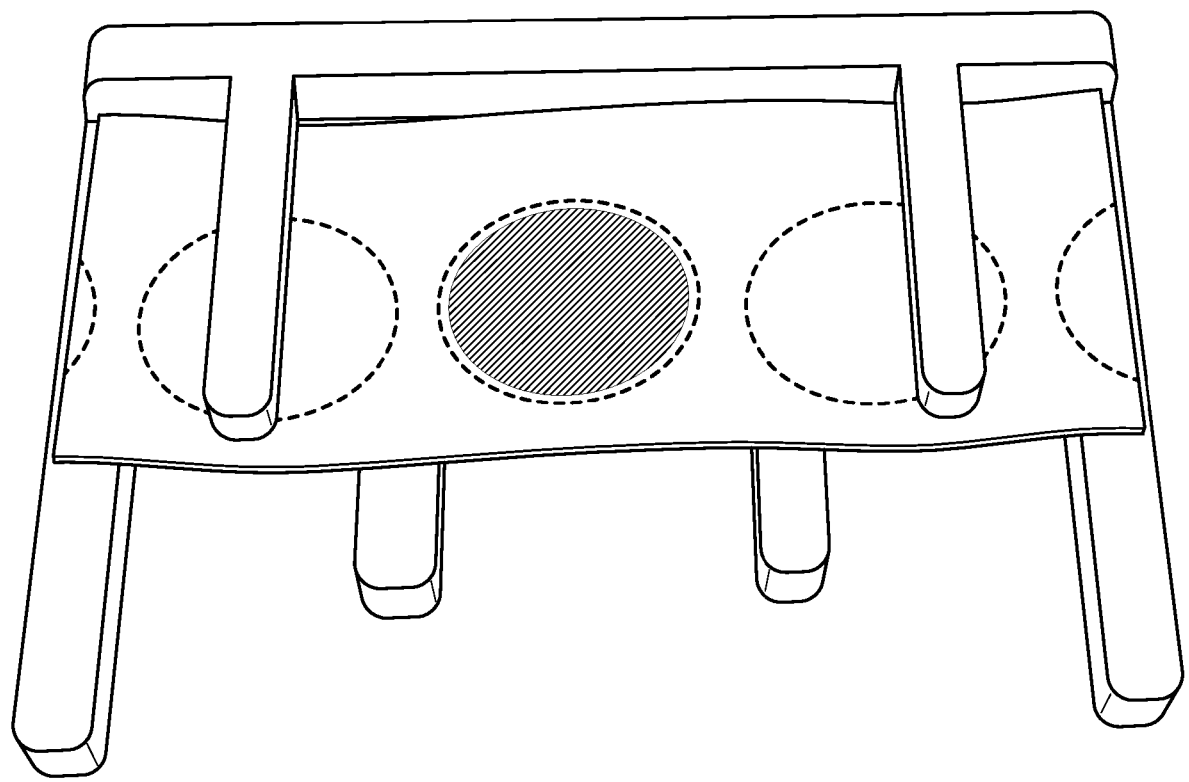
FIG. 9 shows the same type of exemplary plastic support as in FIG. 8 with inserted filter paper, where the support and paper are located in a plastic case. The plastic case may, in some embodiments, have a desiccant located therein.
Figure 10:
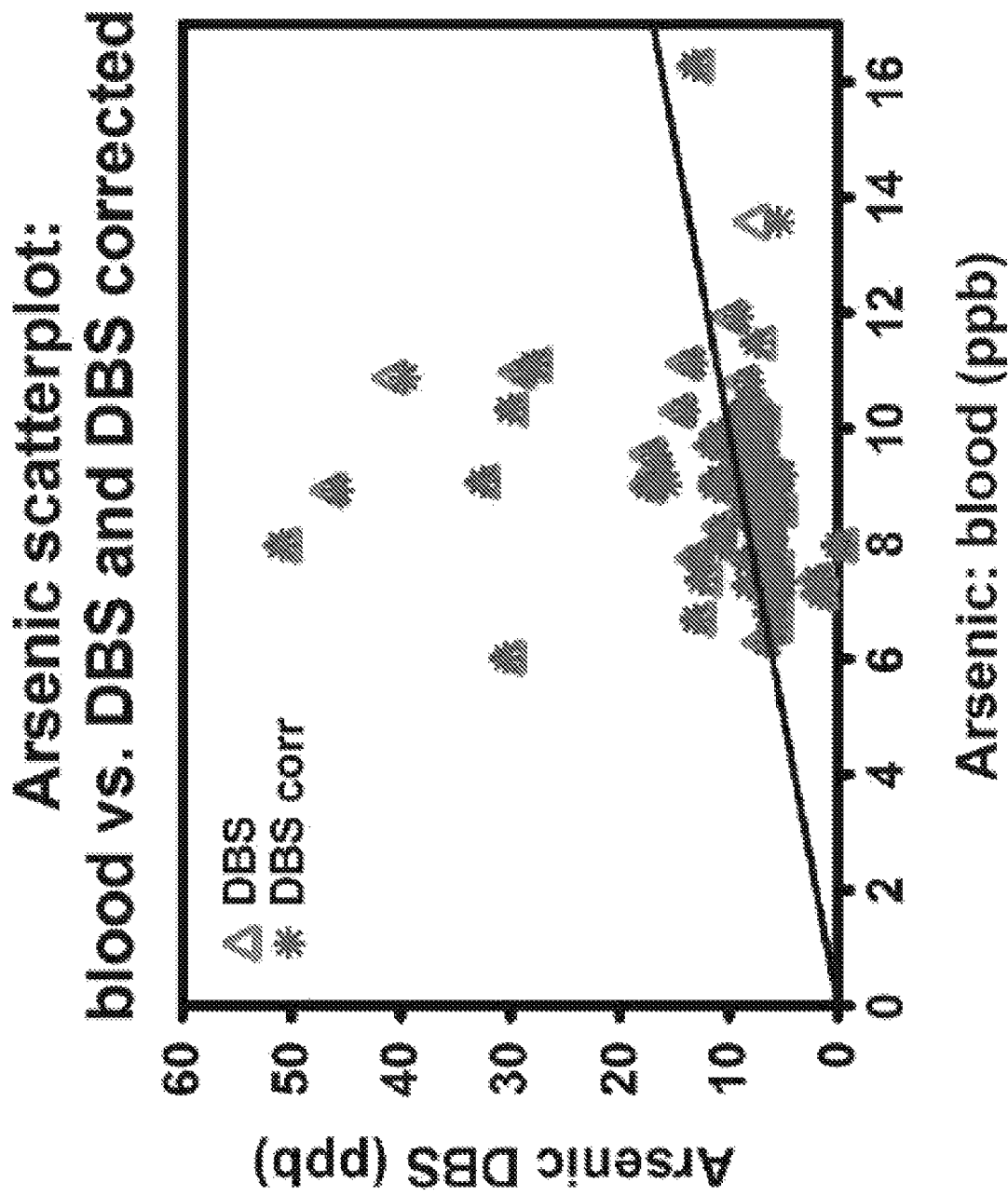
FIG. 10 shows scatterplots of arsenic: venous blood vs. DBS (triangle) and venous blood vs. DBS corrected for within card blank value (star). Straight line indicates perfect agreement.
Figure 11:
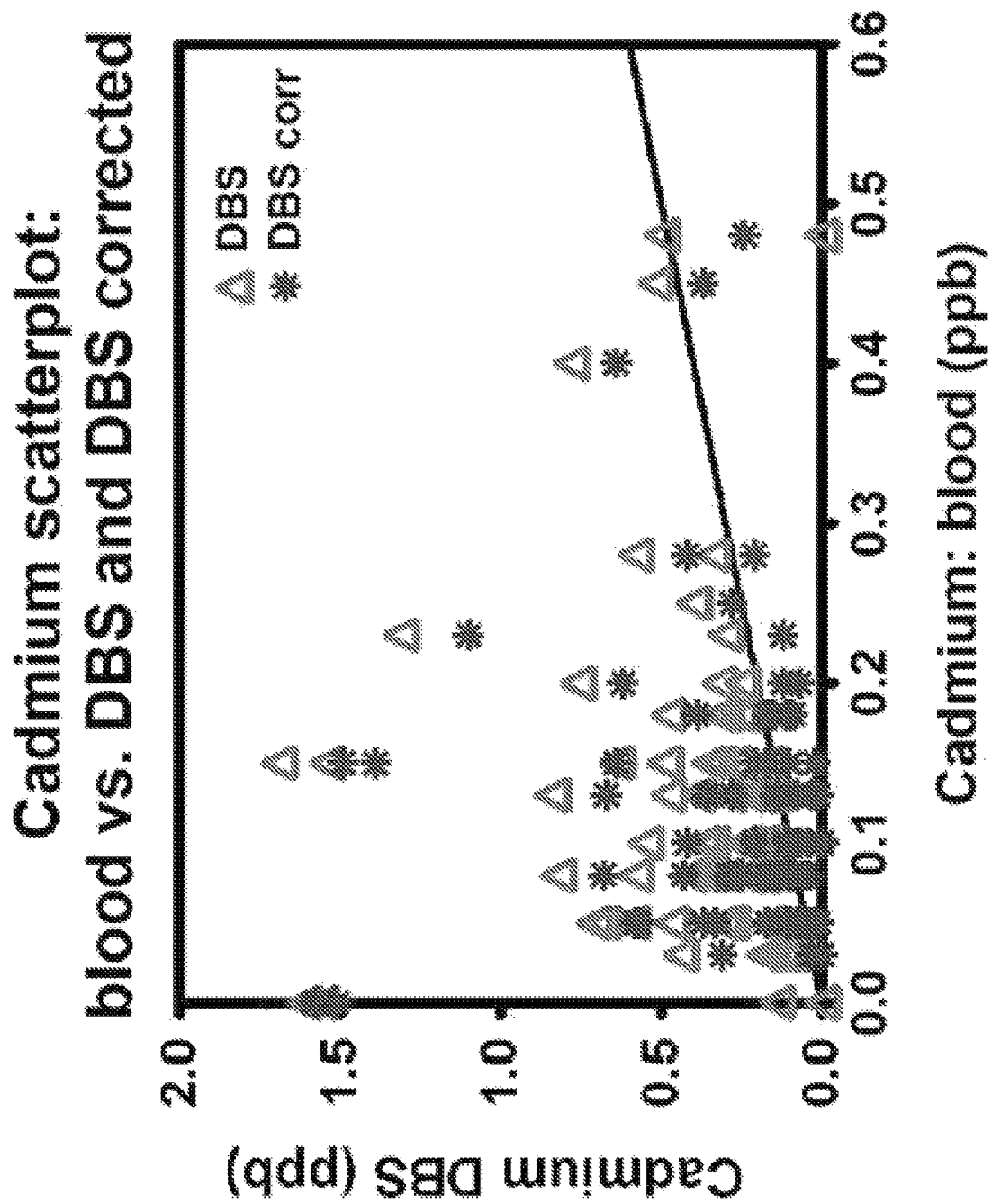
FIG. 11 shows scatterplots of cadmium: venous blood vs. DBS (triangle) and venous blood vs. DBS corrected for within card blank value (star). Straight line indicates perfect agreement.
Figure 12:
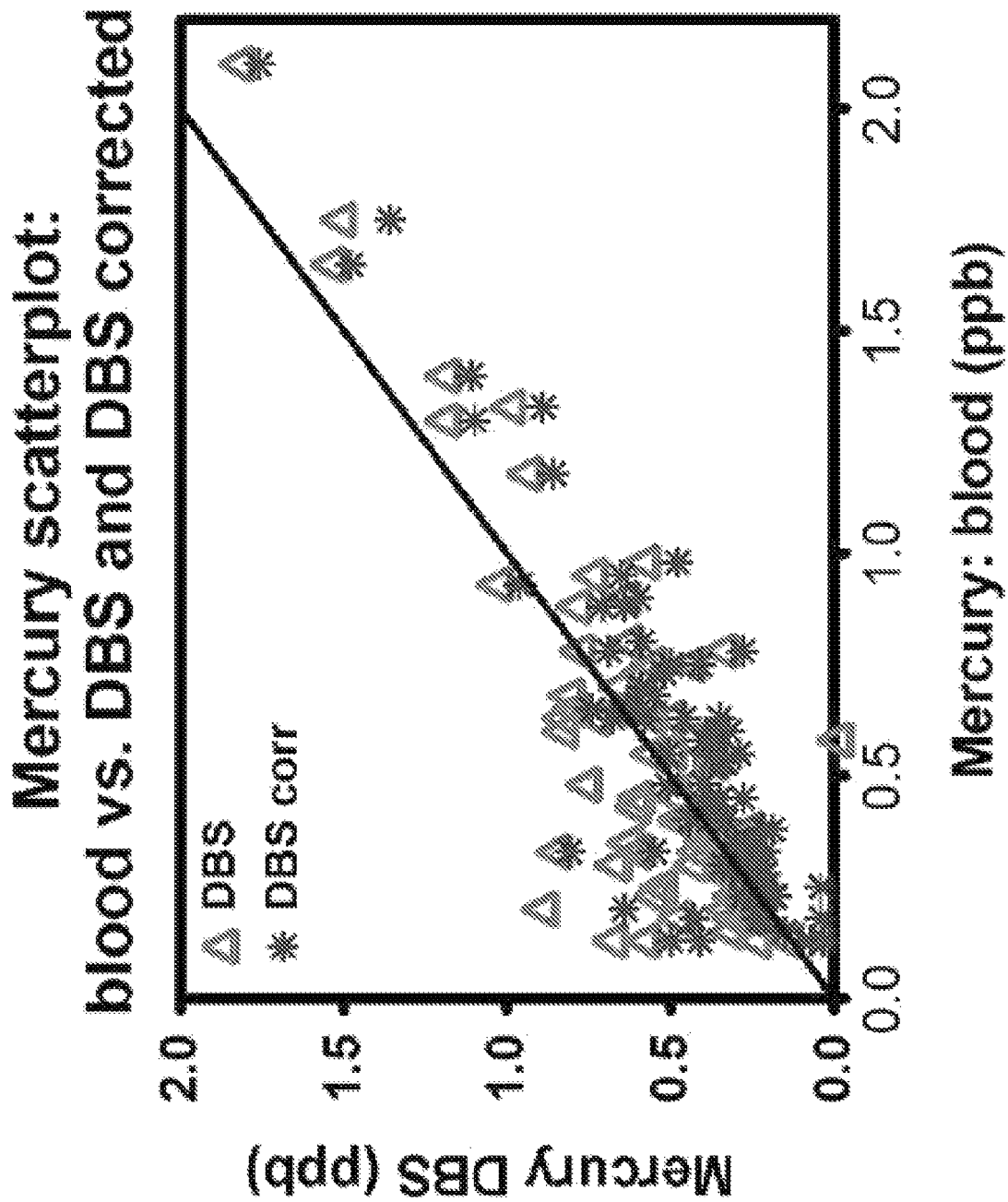
FIG. 12 scatterplots of mercury: venous blood vs. DBS (triangle) and venous blood vs. DBS corrected for within card blank value (star). Straight line indicates perfect agreement.
Figure 13:
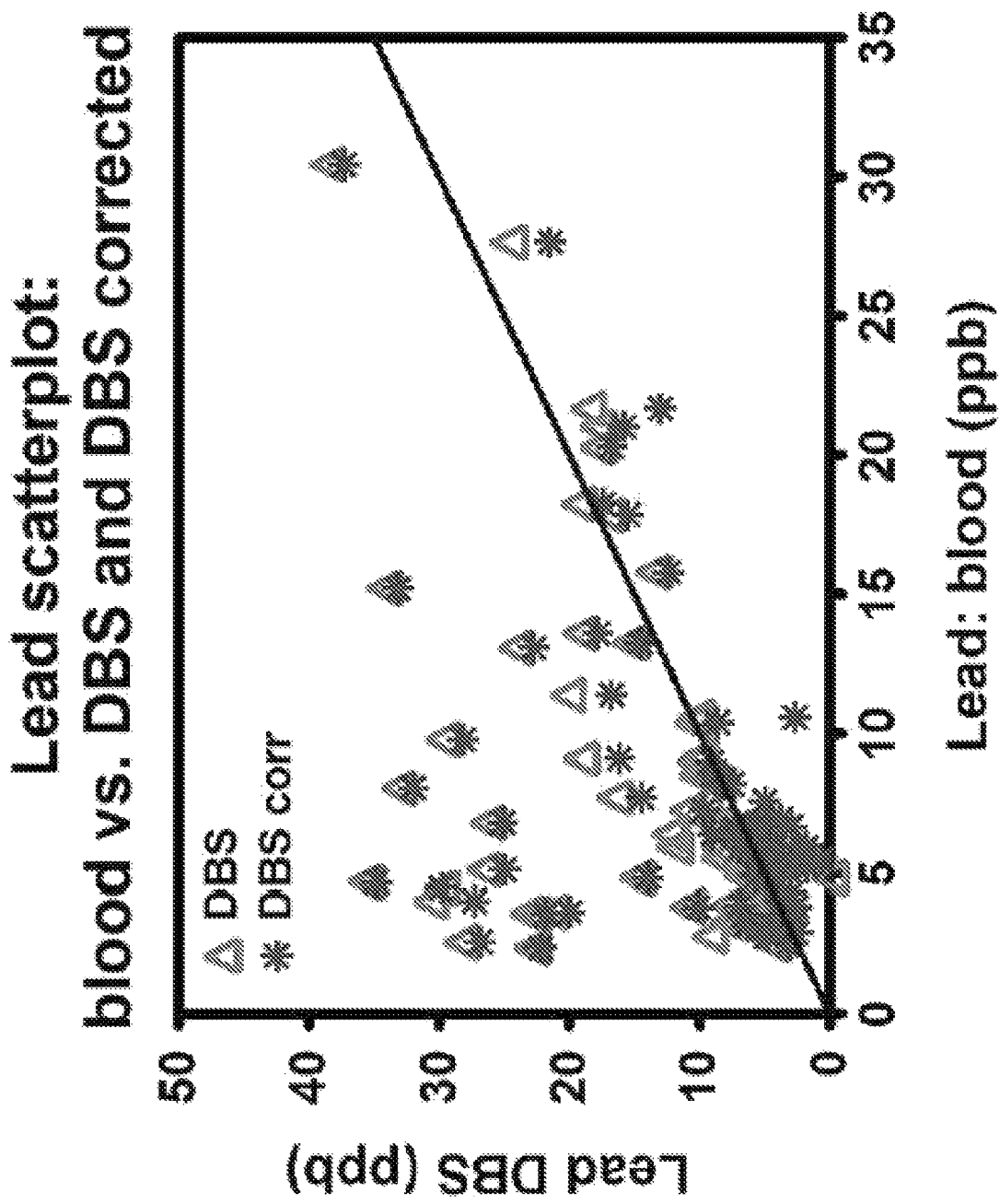
FIG. 13 Scatterplots of lead: venous blood vs. DBS (triangle) and venous blood vs. DBS corrected for within card blank value (star). Straight line indicates perfect agreement.
Figure 14:
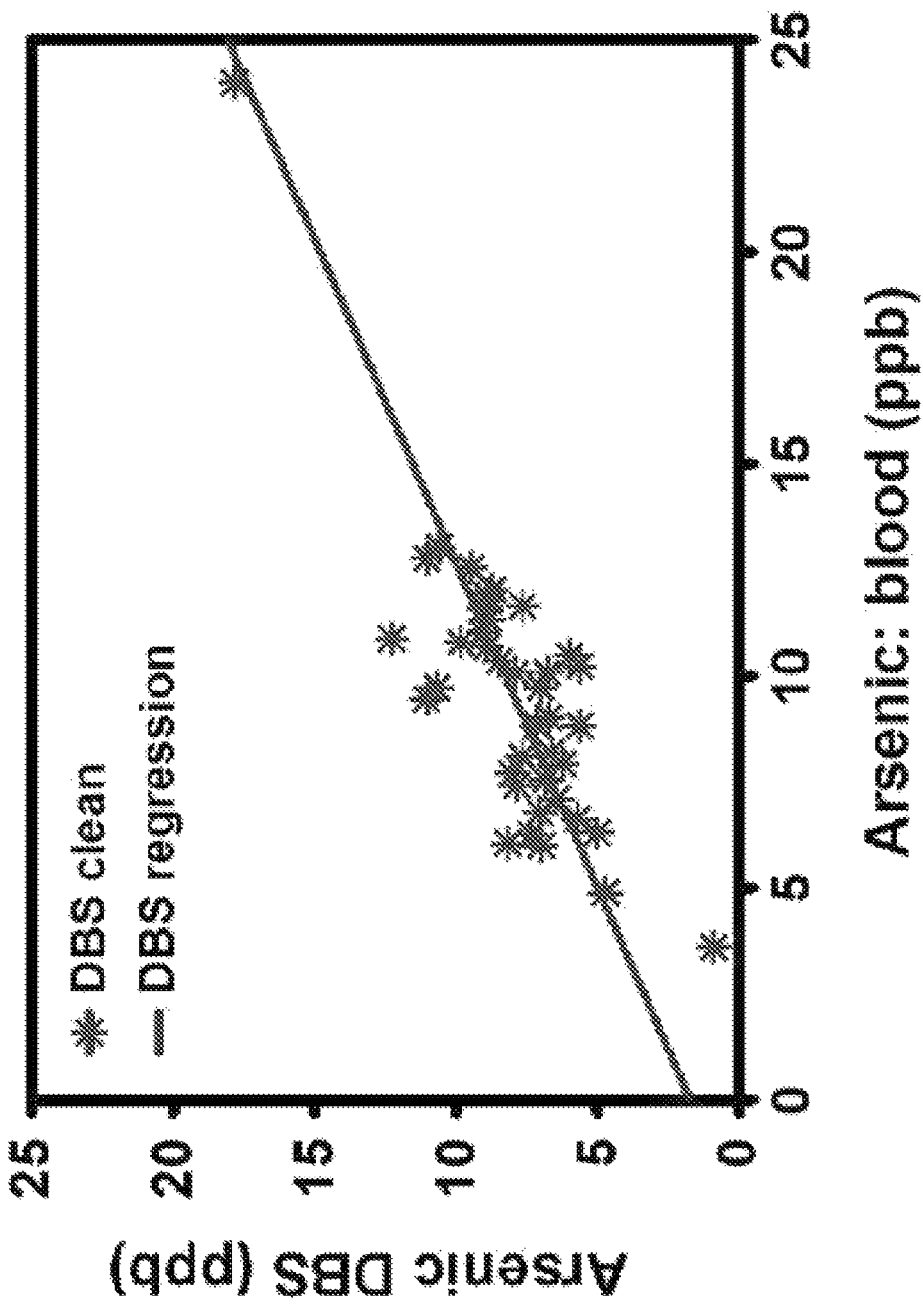
FIG. 14 Scatterplot of lead data: venous blood vs. DBS on pre-cleaned card. Straight line indicates linear regression curve: $y(x)=0.6538(x)+1.733$ ($r^2=0.58$).
Figure 15:
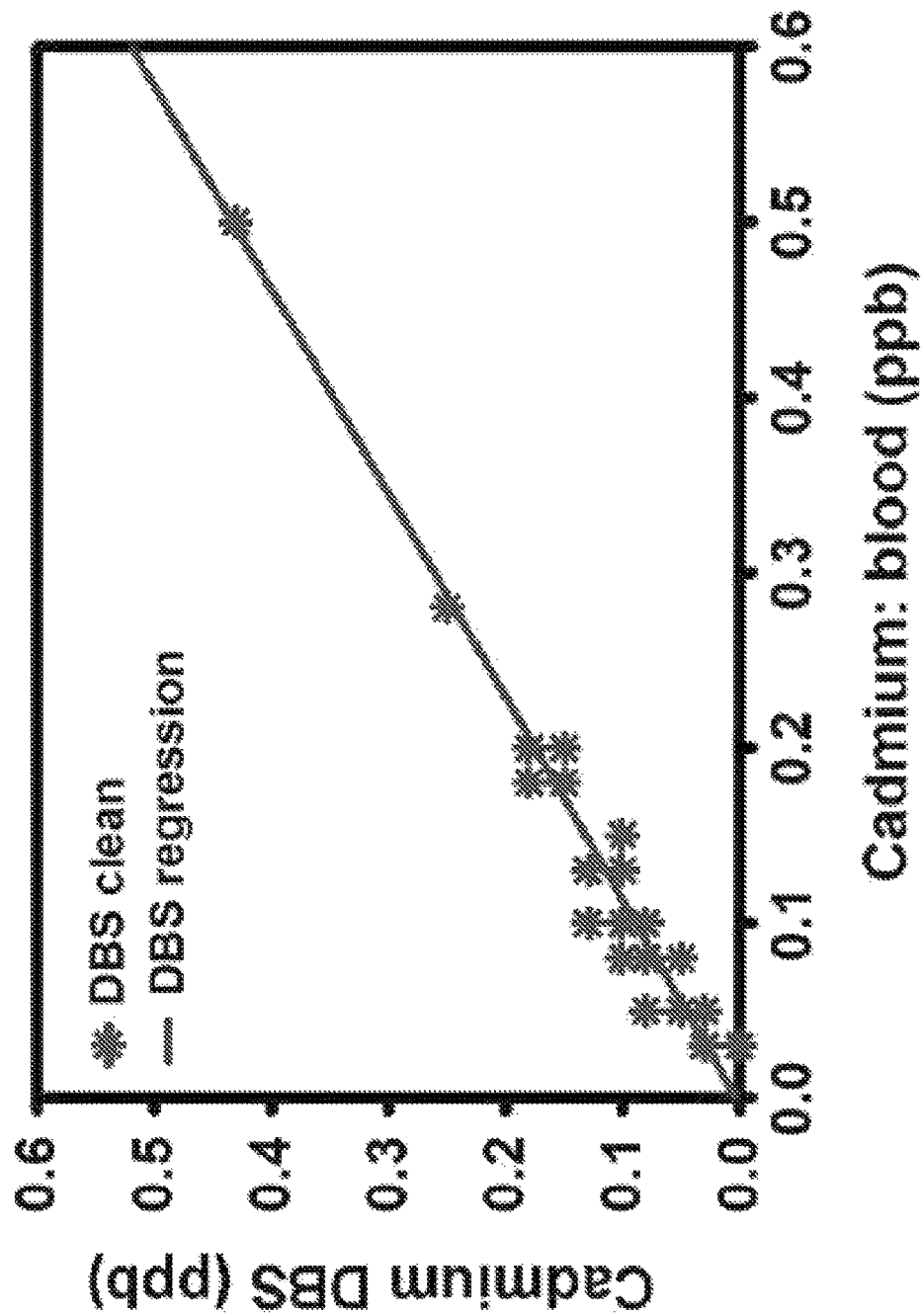
FIG. 15 scatterplot of cadmium data: venous blood vs. DBS on pre-cleaned card. Straight line indicates linear regression curve: $y(x)=0.8606(x)+0.0027$ ($r^2=0.86$).
Figure 16:
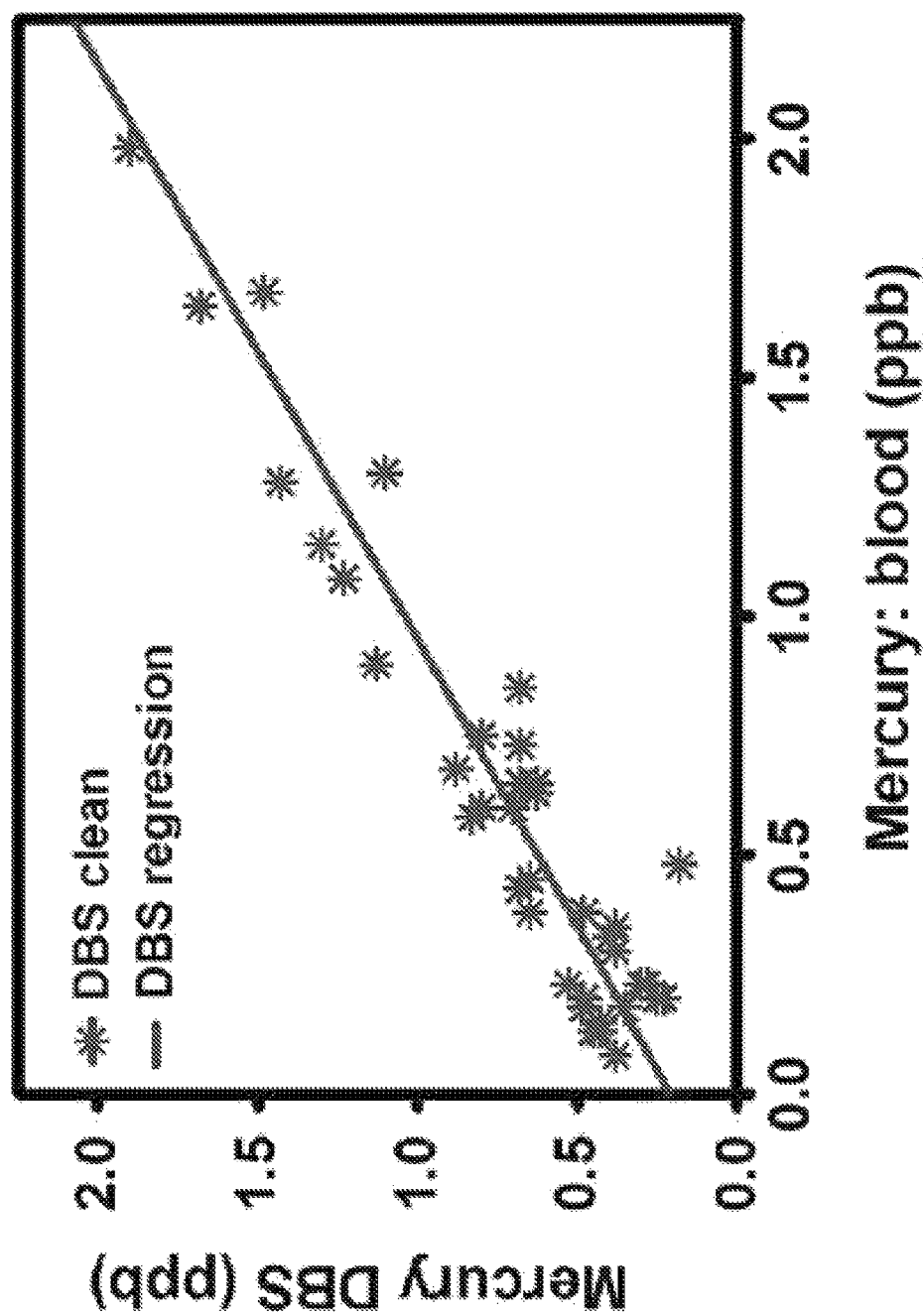
FIG. 16 scatterplot of mercury data: venous blood vs. DBS on pre-cleaned card. Straight line indicates linear regression curve: $y(x)=0.8308(x)+0.2081$ ($r^2=0.66$).
Figure 17:
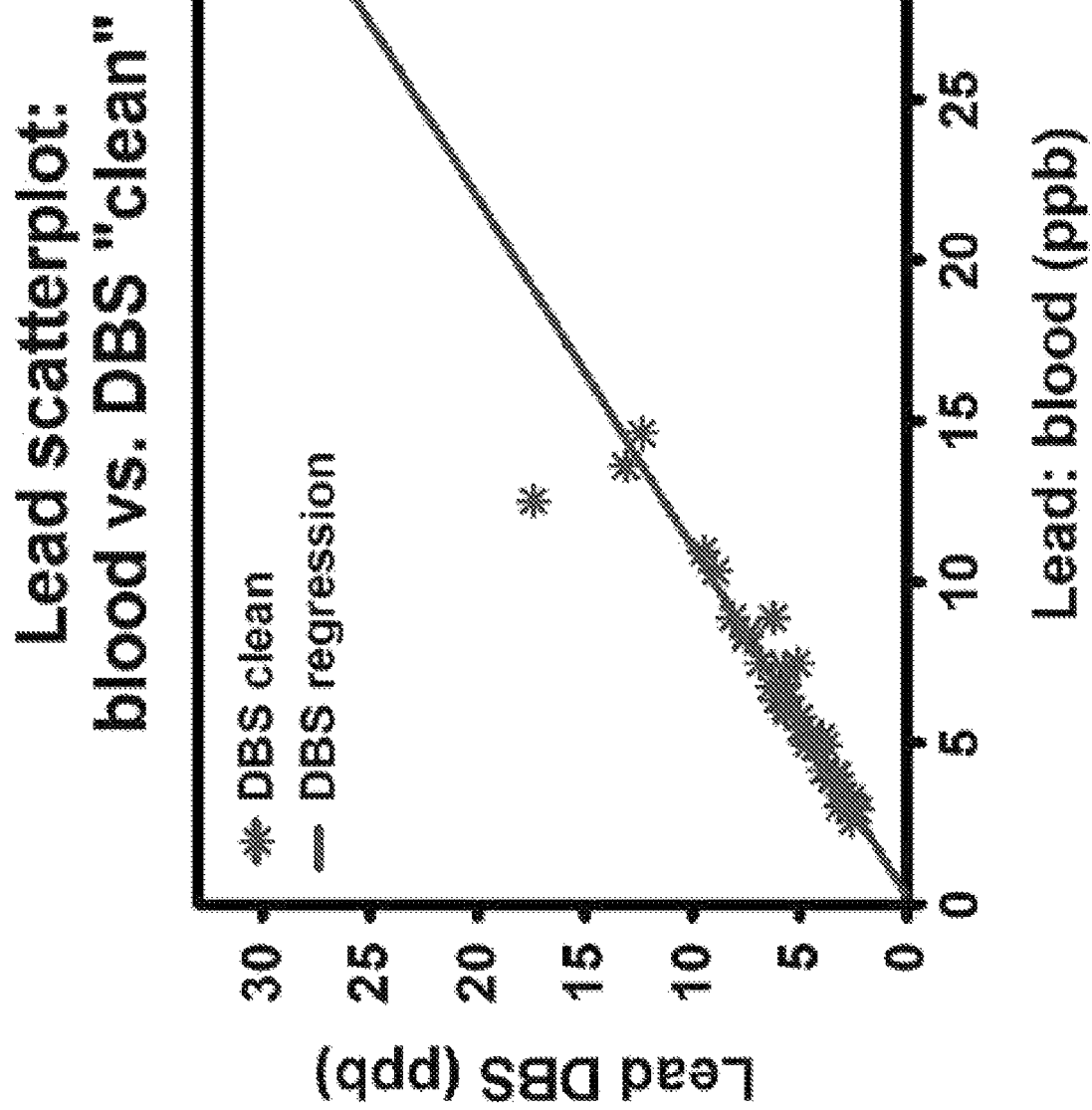
FIG. 17 scatterplot of lead data: venous blood vs. DBS on pre-cleaned card. Straight line indicates linear regression curve: $y(x)=0.9209(x)-0.2085$ ($r^2=0.96$).
Figure 18A:
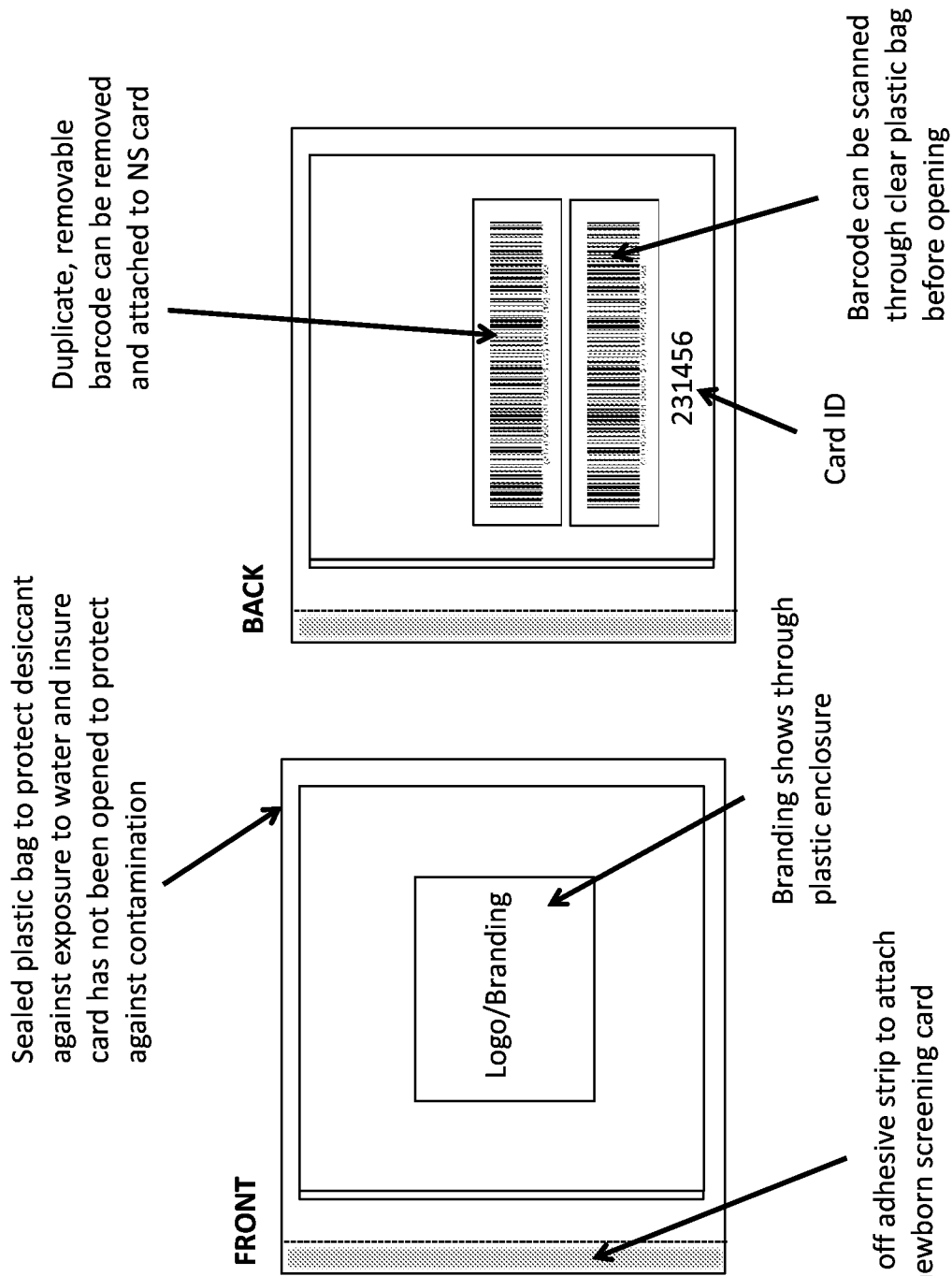
FIGS. 18A, 18B, and 18C illustrate one embodiment collection systems and device as contemplated herein.
Figure 18B:
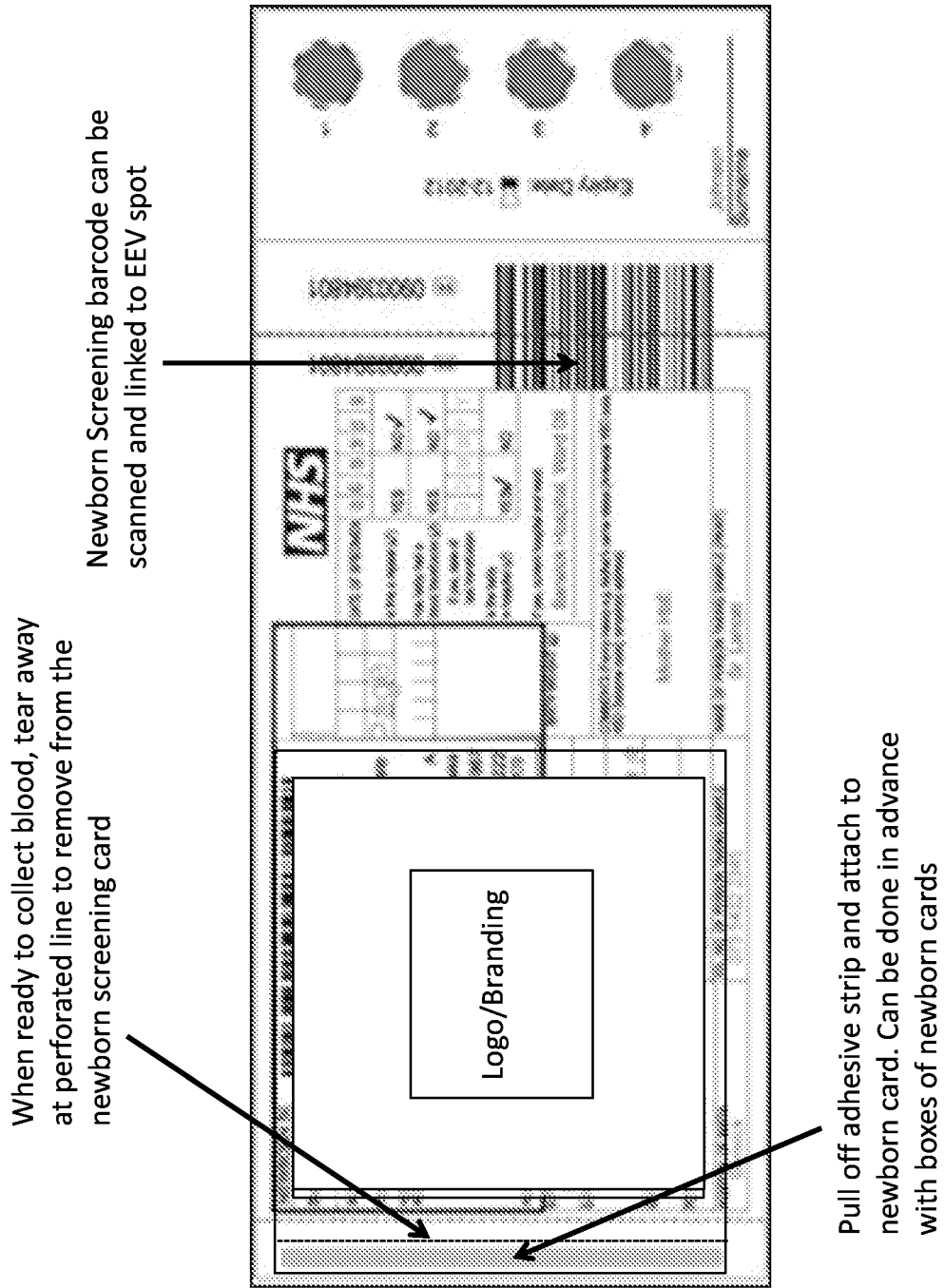
Figure 18C:
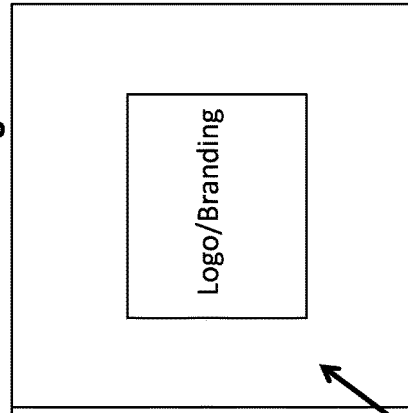
Figure 18C:
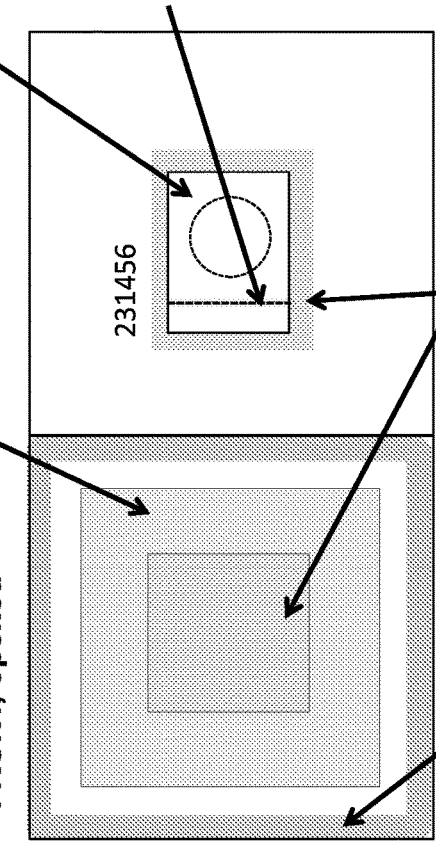
Figure 18C:
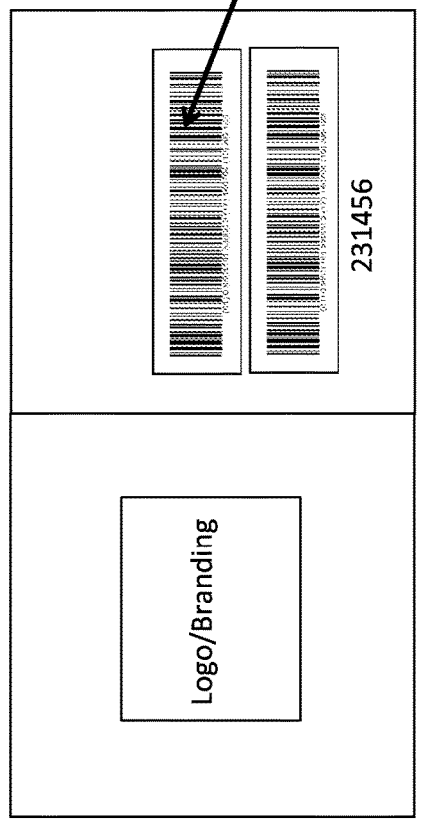
Figure 19A:
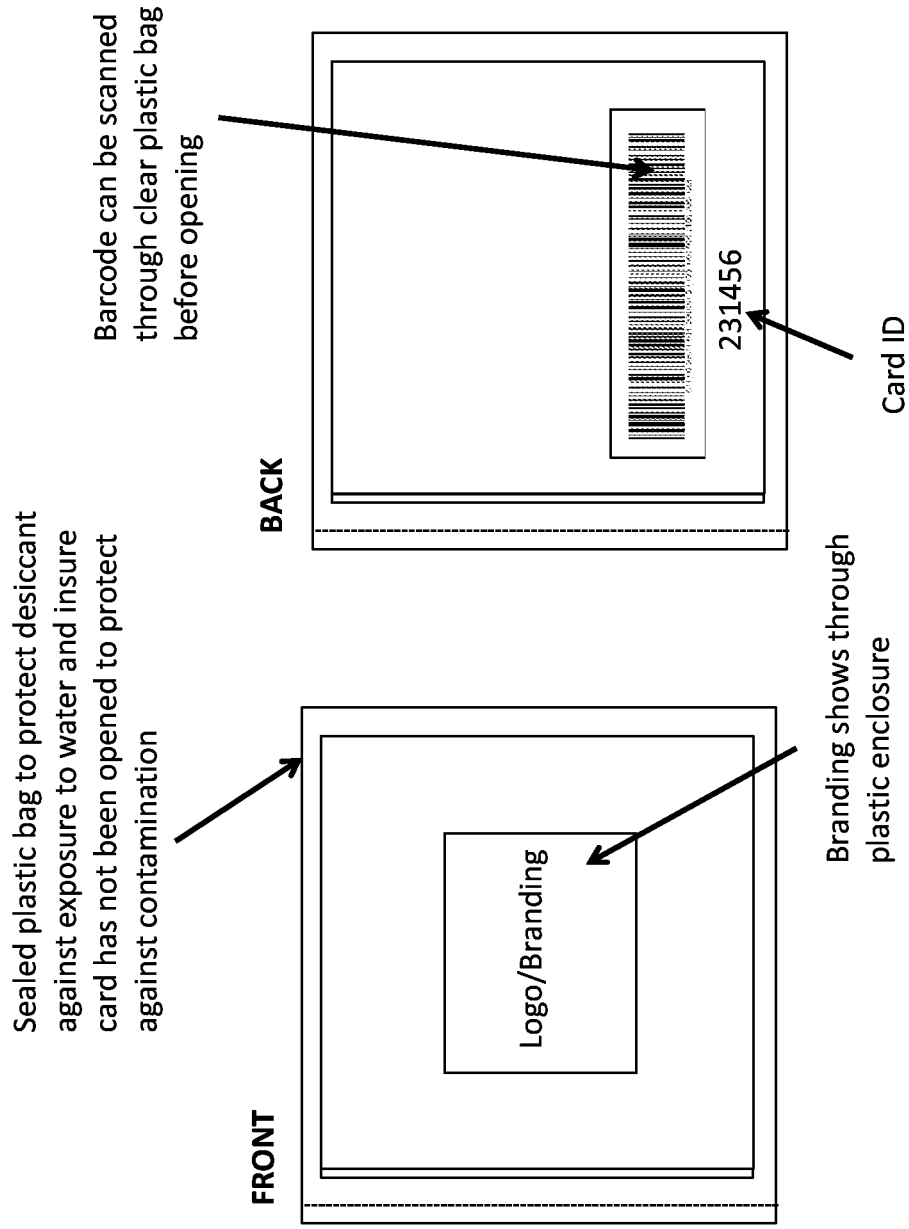
FIGS. 19A, and 19B illustrate one embodiment collection systems and device as contemplated herein.
Figure 19B:
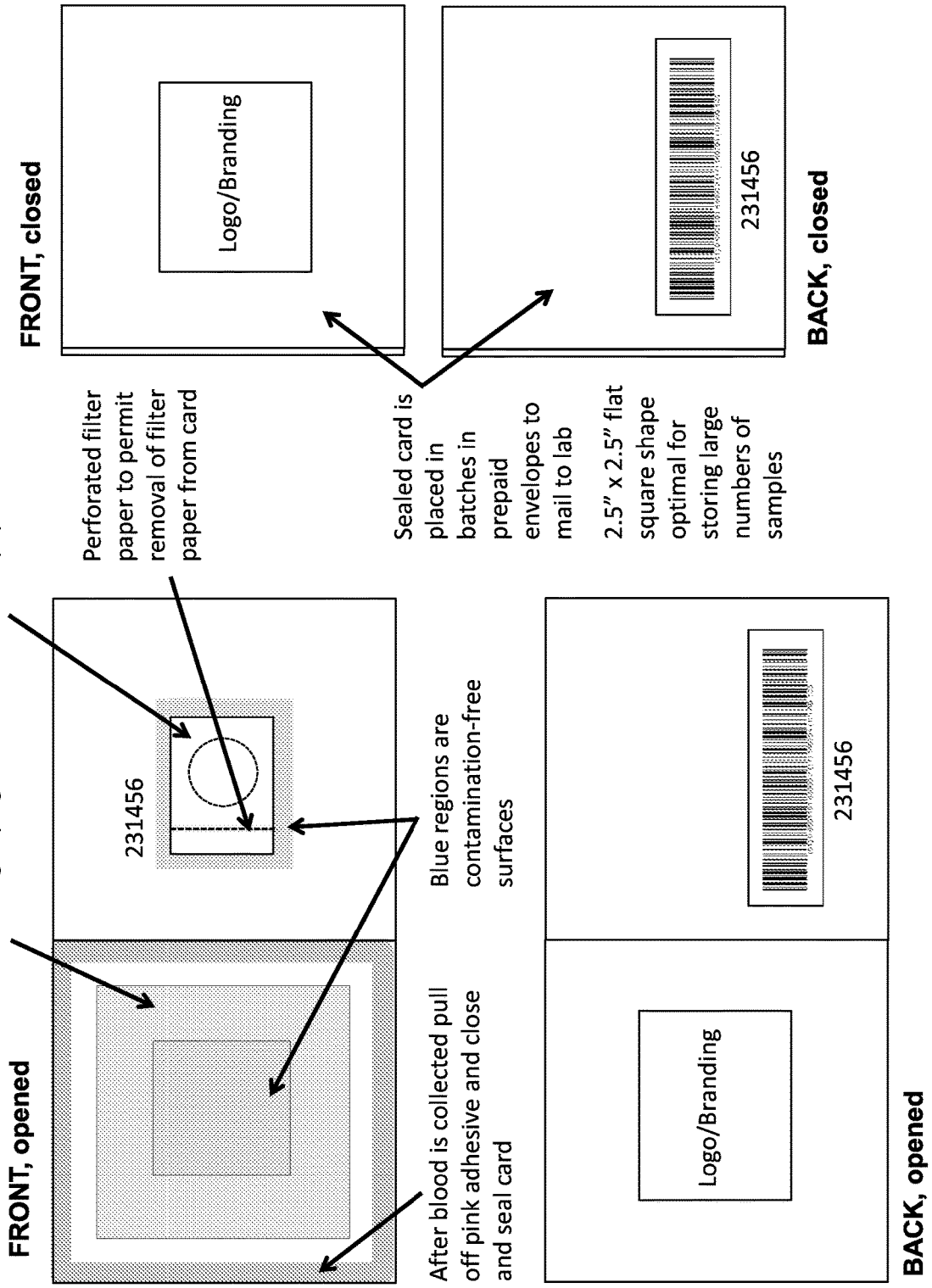

Kits are contemplated herein. The kits may have at least one or more of the following components: a) free or detectably heavy metal free DBS paper; b) free or detectably heavy metal free wipes; c) free or detectably metal free collection case composed of plastic; d) desiccant configured to be inside the collection case (e.g., below blood collection paper); e) plastic DBS ring (e.g., that prevents accidental contamination of paper surface); f) plastic grid or other structure configured to be inserted in collection case under paper (or holding the paper, as shown in FIGS. 7-9), on top of desiccant; g) lancets (sterile disposable finger lancets); and i) an extraction solution containing acetic acid and/or gold.

Figure 6:
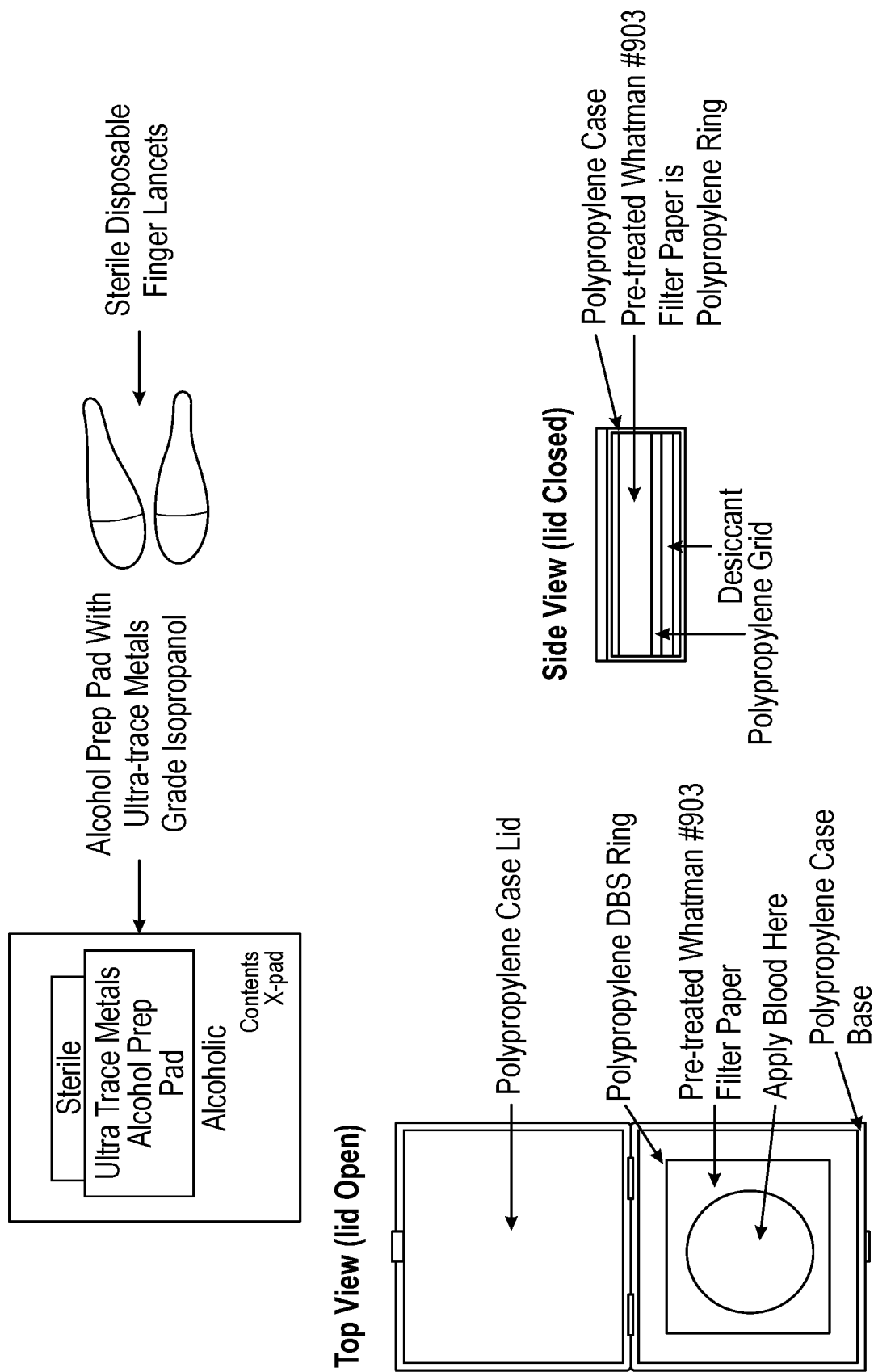
FIG. 6 shows the components for an exemplary heavy metal DBS test kit.

An exemplary kit is shown in FIG. 6. As shown in FIG. 6, an exemplary kit has: an alcohol prep pad with ultra-trace metals grade isopropanol; two sterile disposable finger lancets; a polypropylene collection case (composed of lid and base); a polypropylene DBS ring on top of the paper; pre-treat detectably heavy metal free blood spot paper (e.g., Whatman #903 paper); a polypropylene support grid underneath paper; and a desiccant below the support grid.

Method for detecting heavy metals in DBS also are described herein. Example 1 below discloses a method to quantify heavy metals in DBS that performs at a level that is comparable to venous whole blood-based methods. This simple, and non-invasive blood collection method provides an alternative means of obtaining blood specimens for assessing exposures to toxic metals using a single drop of blood (e.g., collected from a finger or heel prick). Example 1 provides methods to estimate the volume of blood used in a assay for quantifying heavy metals using dried blood mass. The mass of the blood collection device is determined before and after blood collection, strictly controlling temperature and humidity. Initial results show that dried blood mass is highly associated with venous blood volume.

In certain embodiments, the disclosed methods and kits may utilize and/or contain metal-free alcohol wipes (e.g., non-detectable metal in the wipes as measured by conventional, non-extreme methods). Metal contamination from the site of blood collection, and contamination from standard grade isopropanol used in alcohol pads, are potential sources of contamination. In certain embodiments, the wipes are part of a DBS collection kit, and are composed of metal free pads and ultra-trace metals grade isopropanol (or other alcohol) absorbed onto metal-free pads. In certain embodiments, a desiccant is included in the metal free collection case near the blood collection paper. In particular embodiments, a desiccant is sealed inside the metal-free case beneath the blood collection paper to absorb water during the blood drying process. The desiccant may be separated from the sample using a metal-free plastic support (e.g., polypropylene grid). In certain embodiments, during blood collection, the lid on the collection case will be opened briefly during blood collection and then immediately sealed following blood application to the paper (or other blood collection device) to avoid contamination. In certain embodiments, the kits and devices of the present invention are collected outside the clinic (e.g., home, in the field, etc.) and are shipped to a lab (e.g., at room temperature) in an envelope (e.g., flat envelope).

EXAMPLES

The following Examples are illustrative and are not intended to limit the scope of the claimed subject matter.

Example 1—Heavy Metal Detection in Dried Blood Spots

This example describes heavy metal detection in dried blood spots and specifically describes a targeted extraction and analytical procedure optimized for specifically quantifying As, Pb, Hg, and Cd in DBS specimens. Major features of this protocol include: 1) the use of a one-batch extraction procedure to avoid contamination and analyte loss during transfer and filtration steps, 2) the addition of gold (Au) in the extraction solution to amalgamate Hg and enhance recovery and prevent loss of Hg throughout the analytical procedure, 3) normalization of dried blood mass to more precisely estimate relative blood volumes, 4) the use of paired filter paper blanks for all DBS samples to evaluate background contamination in the Whatman #903 Protein Saver cards, and 5) use of an organic acid (ultra-trace metals grade acetic acid) to enhance the signal for As.

All samples were excised using ceramic scissors (VWR, Atlanta, Ga.) that were acid washed in a 5% acetic acid (v/v) solution overnight prior to use, and samples were handled with acetic acid washed Teflon tweezers. Entire DBS specimens were excised using the printed guidelines on the blood collection cards as a guide. The volume of blood in an intact DBS is approximately 60 µl. However, to account for blood volume variation between samples, the dried mass of each sample was normalized to the mean mass of all of the excised samples. A similar approximate size of a blank filter paper is excised from each card near each blood sample to account for background metal contamination in the filter paper. The mass of each blank was also normalized to the mean mass of all of the excised blanks. DBS and filter paper blanks were weighed in 15 ml metal-free polypropylene centrifuge tubes (VWR, Atlanta, Ga.). An extraction solution was prepared using 5% ultrapure grade acetic acid and 0.01% ultrapure grade Triton X-100 (Fisher Scientific, Pittsburgh, Pa.) in 18.2 mΩ deionized water. Two hundred ppb of Au was added to amalgamate Hg and prevent analyte loss throughout the procedure (Inorganic Ventures, Christiansburg, Va.). One and a half ml of extraction solution was added directly to each vial. Five ppb of indium, bismuth, and yittrium were added to the extraction solution as internal standards (Inorganic Ventures, Christiansburg, Va.). DBS samples and filter paper blanks were centrifuged at 3600×g for 2 minutes and incubated for 90 minutes at room temperature on a shaker table at 300 rpm. Prior to analysis the centrifuge tubes were inverted and manipulated to adhere the filter paper to the side of the tubes in order to remove them from the blood extracts. Filtration was avoided to prevent contamination and analyte loss.

Concentrations of As, Pb, Hg, and Cd were quantified using a ThermoFisher X Series II Inductively Couple Plasma Mass Spectrometer (ICP-MS). The instrument detection limits were determined to be in the low ppt range for each element. Metal concentrations were quantified based on a five-point calibration curve for each analyte. For Pb, three isotopes were scanned and summed (m/z: 206, 207, and 208). As, Hg, and Cd, were quantified using single isotopes with m/z of 75, 202, and 111, respectively. In addition to the samples and paired card blanks, quality control samples were run along with each batch, consisting of a matrix blank, a trace element whole blood reference (ClinChek, Munich, Germany), and a trace element whole blood reference spiked onto Whatman #903 filter paper.

For method validation, 85 matched venous whole blood and finger stick DBS samples were collected at a Hospital in Illinois. Volunteers were between the ages of 1 and 21. Venous blood samples were collected in metal-free vacutainers, and DBS samples were collected using Whatman #903 Protein Saver cards. DBS were dried at room temperature for four hours and placed in plastic bags with desiccant packs. All samples were frozen at −80° C. until shipped to the Northwestern Laboratory for Human Biology Research on dry ice.

Concentrations of heavy metals in matched whole blood and DBS samples are provided in FIG. 1. Correlations between whole blood and DBS samples were very low for Pb, Cd, and As. Mercury had the strongest correlation between samples with an $R^2=0.35$. However, these results were skewed by a single outlier that contained elevated levels of Hg in the DBS sample. Concentrations of heavy metals were also quantified in pair-wise blank DBS samples (data not shown). Lead concentrations in the blank samples were significant. However, Pb contamination was determined to be non-homogenously distributed across the cards. Background contamination of Hg, Cd, and As were mostly low, but significant given the trace level concentrations of these metals that are generally found in blood. Pair-wise subtraction of the blank samples from the DBS modestly improved the correlation between Hg in the matched venous whole blood and DBS samples, increasing the $R^2$ from 0.35 to 0.52. However, using pair-wise subtraction did not significantly improve the correlation between venous blood and DBS samples for Pb, Cd, and As, which were 0.11, 1.5× $10^{-5}$, and 0.04, respectively.

Overall, heavy metal contamination in the Whatman #903 filter paper was significant, and alternative blood collection methods are required for accurately quantifying trace level heavy metals in DBS samples.

A method was developed to pretreat the Whatman #903 filter paper to remove heavy metals prior to blood collection. Sections of each card containing the printed blood collection guides were excised with ceramic scissors. Three cards were placed in IL of 5% ultratrace metals grade hydrochloric acid and 5% ultratrace metals grade nitric acid in 18.2 mΩ deionized water (VWR BDH Aristar Ultra, Chicago, Ill.). Metal extraction was performed in Nalgene Low Metals bottles (Fisher Scientific, Pittsburgh, Pa.) at room temperature on a shaker table for 90 minutes at 300 rpm. Following metals extraction the cleaned cards were rinsed twice using IL of 18.2 mΩ deionized water. The extraction bottles were then filled with an additional IL of 18.2 mΩ deionized water and placed on a shaker table for 15 minutes at 300 rpm. The cards were then rinsed an additional two times using IL of 18.2 mΩ deionized water for each wash. The cleaned filter paper was then removed using acid washed Teflon tweezers and dried overnight suspended within a fume hood.

Pretreated filter paper samples were extracted and analyzed using the method described above. For comparison, untreated Whatman #903 cards were also excised and analyzed the same conditions and same amount of sample.

Figure 2:
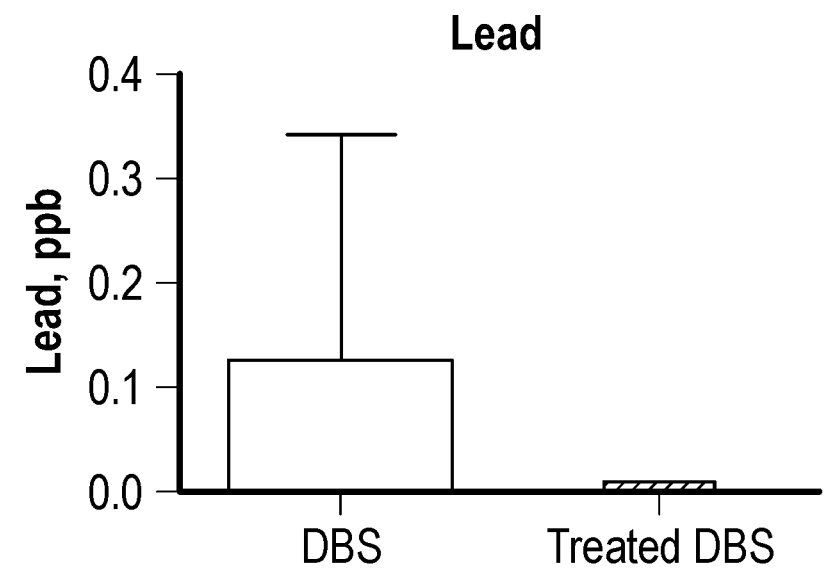
FIG. 2 shows results from Example 1 below, providing concentrations of Pb and Cd measured in treated and untreated Whatman #903 filter paper. After treatment all metals were undetectable.
Figure 2:
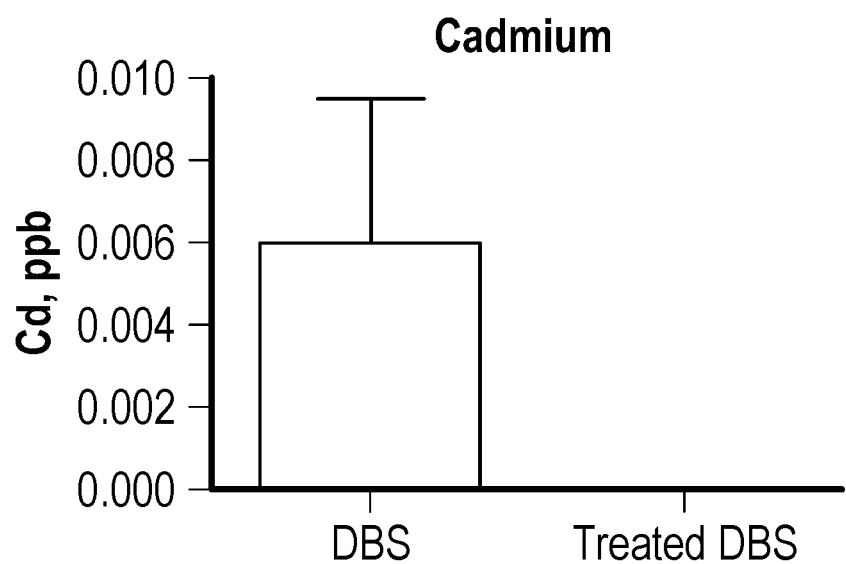

Concentrations of Pb, Cd, Hg, and As were below the level of detection in all pretreated samples. Differences between the treated and untreated filter paper was most significant for Pb and Cd (FIG. 2). This procedure was effective in reducing all trace levels of heavy metals below the instrument detection limit. An experiment was performed to assess the performance of the pretreated filter paper for quantifying trace level heavy metals in blood. Whole blood samples (described above) were spotted onto cleaned filter paper in 60 µL aliquots. All DBS samples were dried overnight (n=54). Matched venous whole blood and DBS samples were analyzed for Pb, Cd, Hg, and As using the method described above.

Figure 3:
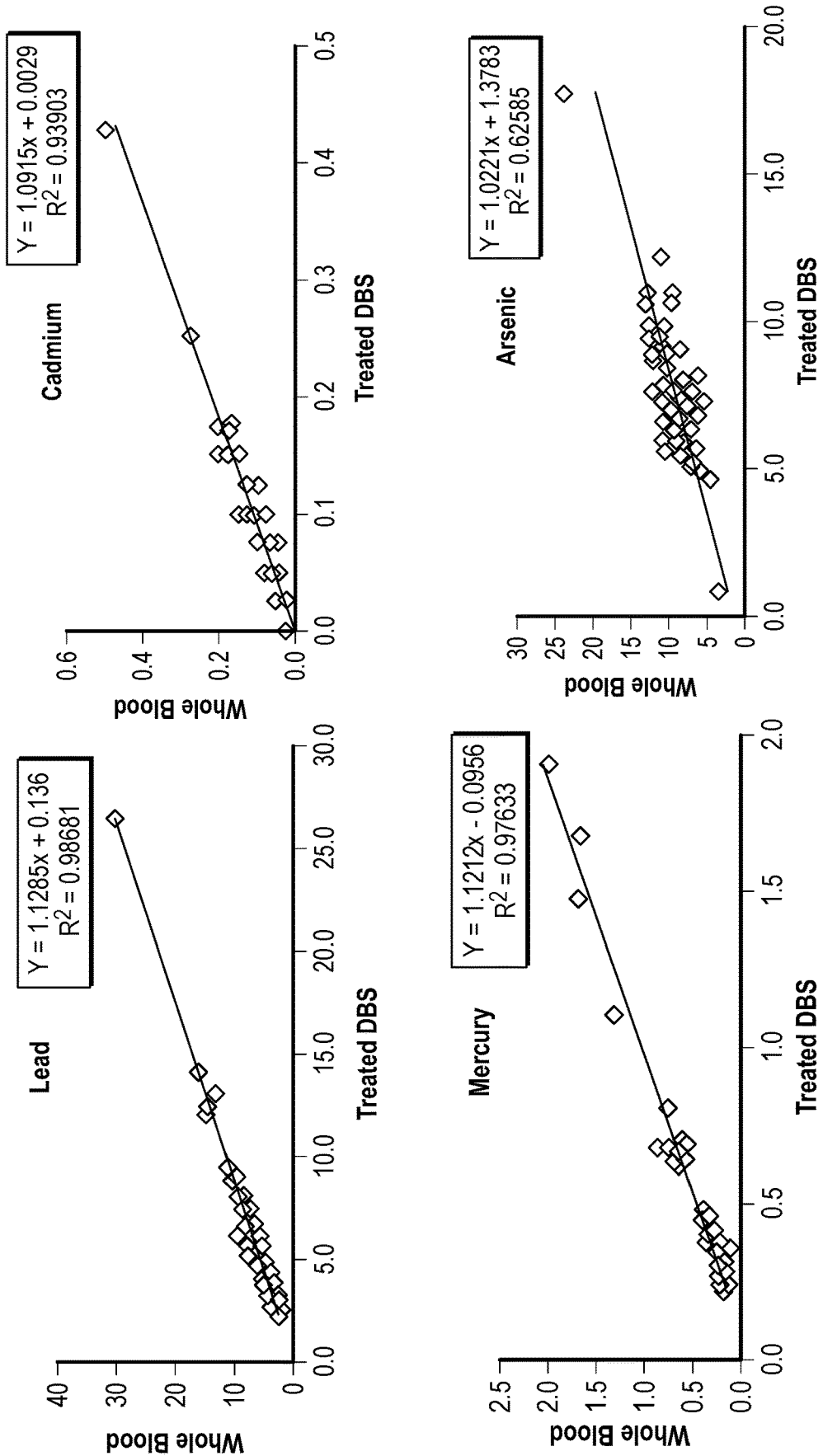
FIG. 3 shows results from Example 1 below, providing scatterplots and regression analysis of the association between heavy metals obtained from matched venous blood and DBS samples collected on pretreated Whatman #903 filter paper.

Pretreatment of the Whatman #903 filter paper to remove heavy metals prior to blood application did not appear to alter the blood absorbance and distribution properties of the filter paper. As with untreated cards, 60 µL of blood completely filled the printed blood collection guidelines. Scatterplots of the matched venous blood and DBS samples using pretreated filter paper are provided in FIG. 3. Quantification of heavy metals in DBS collected on pretreated Whatman #903 filter paper provided comparable precision to the venous blood "gold standard" method.

For relative comparisons of heavy metals in DBS, such as in case control studies, blood volumes can be normalized by adjusting the excised mass of a DBS to the mean mass of all of the samples within a study (using the printed guidelines on the Whatman #903 paper to excise approximately the same volume from each sample). However, for population screening, absolute concentrations of heavy metals are of interest rather than relative values.

Figure 4:
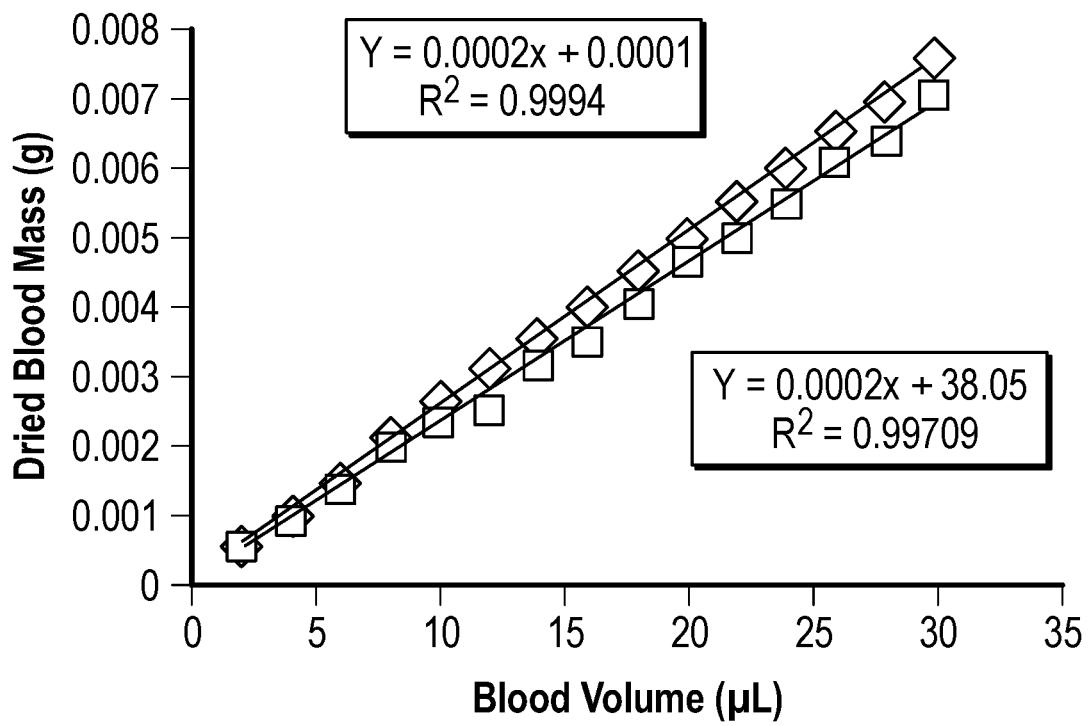
FIG. 4 shows results from Example 1, providing the association between dried blood mass and venous blood volume. Male sample points are smaller diamonds, while female sample points are larger squares.

To estimate blood volumes in DBS samples, the mass of the Whatman #903 filter paper samples was determined before and after blood application. After blood was applied to the filter paper, all samples were completely dried prior to obtaining the post-blood application masses. To determine the association between dried blood mass and venous blood volume, measured concentrations of venous blood was applied to Whatman #903 filter paper in volumes ranging from 2-30 µL. The results from this experiment are provided in FIG. 4.

Figure 5:
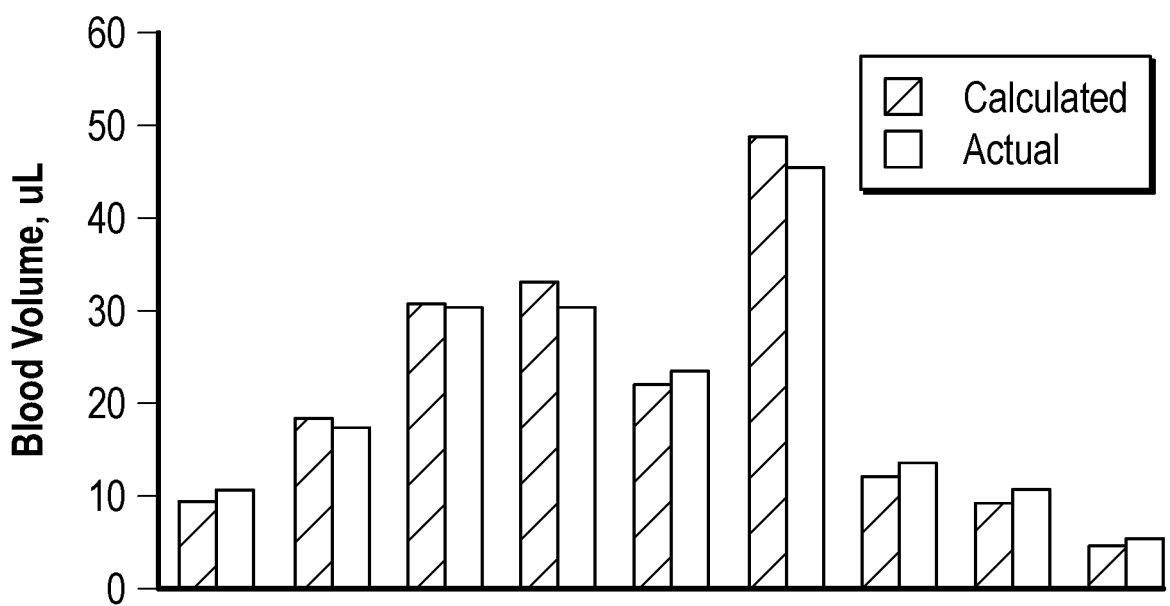
FIG. 5 shows results from Example 1, providing an estimation of venous bloodvolume from dried blood mass.

Dried blood masses and venous blood volumes were highly correlated. Minor differences were observed between males and females. Validation experiments were performed to determine how precisely venous blood volumes could be estimated from dried blood mass using DBS samples that were spotted with known blood volumes of blood, that were blinded to the analyst. Blood was applied at different volumes using whole blood collected from nine male and female volunteers. Blood volume estimations were calculated using averages of male and female values from FIG. 4. Results are provided in FIG. 5. These results suggest that dried blood mass can be used to accurately estimate venous blood volume.

Example 2—Use of Dried Blood Spots for Estimating Exposures to Heavy Metals in Epidemiological Research Reference is made to Funk et al., "Use of Dried Blood Spots for Estimating Children's Exposures to Heavy Metals in Epidemiological Research," *J. Environ. & Analyt. Toxicology* 2015, S7, ISSN: 2161-0525, published on Jul. 24, 2015 and incorporated herein by reference in its entirety.

ABSTRACT

Background: Children's exposures to arsenic (As), lead (Pb), mercury (Hg), and cadmium (Cd) are of particular concern in early-life. Exposures to heavy metals are traditionally measured in whole venous blood, which is costly and invasive. As an alternative we describe a method for quantifying As, Pb, Hg, and Cd in dried blood spot (DBS) samples.

Objectives: To validate a method for quantifying levels of As, Pb, Hg, and Cd in finger-stick DBS samples. Background metal contamination in blood collection cards poses a challenge for quantifying heavy metals in DBS samples. Here we report a method to remove background contamination from the filter paper prior to blood collection to improve assay precision.

Methods: Matched samples of venous blood and finger-stick DBS samples were collected from 82 children ages 1-21. Whole venous blood samples were also applied to pre-cleaned and untreated blood collection cards. All samples were analyzed for As, Pb, Hg, and Cd using inductively coupled plasma mass spectrometry (ICP-MS).

Results: Matched venous blood and finger-stick DBS samples from untreated cards were significantly correlated, but with relatively weak R2 values of 0.083, 0.186, 0.498, and 0.022 for As, Cd, Hg, and Pb, respectively. When blood collection cards were decontaminated prior to blood collection the correlations between venous blood and DBS samples were highly significant, with R2 values of 0.66, 0.99, 0.98, and 0.94 for As, Pb, Hg, and Cd, respectively.

Conclusions: Standard blood collection cards contain significant and highly variable background levels of heavy metals. Once blood collection cards are treated to remove residual contamination, DBS sampling can be used as a minimally-invasive alternative to venipuncture to estimate exposures to toxic metals.

INTRODUCTION

The discipline of environmental exposure science is intricately linked with epidemiological investigations for protecting public health [1,2]. Historically, methods were focused on measurements of environmental media used to estimate potential human exposure through various uptake pathways. More recently, there has been a shift towards incorporating biomarker data as a more direct link to exogenous exposures through measurements from human biological media such as blood, breath, and urine for exploring the concept of the human exposome-representing all chemical exposures from conception throughout life [3-5]. The combined use of biomarkers of exposure and biomarkers of effect has also become a central theme for linking the external environment to potential adverse health outcomes [6-8]. There are now large databases such as the U.S. National Health and Nutrition Examination Survey (NHANES), the German Environmental Survey (Ger ES), The Korea National Health and Nutrition Examination Survey (KNHANES), and the Canadian Health Measures Study (CHMS) that are making such data mining readily available to the research community [9-12]. These are based on detailed analyses of thousands of "snapshot" measures from stratified random selections of subjects from the general populations of the respective countries. Supplementing such information with repeat measures and many more subjects will provide an ever-improving statistical understanding of environmental exposures, onboard dose, environmental metabolomics, and ultimately public health sustainability [13-16].

Currently, a major issue is the exposure of children to heavy metals, which are of particular concern early in development. In fact, As, Pb, Hg, and Cd are listed as the 1st, 2nd, 3rd, and 7th most important hazardous substances on the Agency for Toxic Substances and Disease Registry's 2013 CERCLA priority list of 275 substances, respectively. Exposure to heavy metals can occur through a variety of exposure routes, including inhalation as dust and fumes [17,18], and ingestion from food and water [19-21], and can cause a wide spectrum of health problems including convulsions, coma, renal failure, injuries to the lungs and neurologic system, memory loss, delirium, diabetes, kidney damage, and a variety of cancers [22]. In addition, heavy metals can cross the placental barrier during pregnancy resulting in toxic exposures during highly susceptible periods of fetal development [23-25]. Yet, the health impacts of exposures to toxic metals during all stages of early development are not well understood due to the paucity of in vivo human data. Thus, additional studies are critically needed using emerging exposure assessment tools.

Ideally, exposure to toxic metals should be monitored over time to evaluate changes that precede adverse health events and follow environmental exposures longitudinally. However, collecting blood samples with venipuncture in community-based research suffers from logistical obstacles (medical personnel, specialized containers, infectious wastes, refrigeration, etc.) and also from low acceptance in pediatric and younger populations [26]. As an alternative, dried blood spots (DBS)-drops of capillary whole blood collected from a finger or heel stick—can be used as a minimally-invasive and low cost alternative to invasive venipuncture [27].

The use of DBS sampling for screening newborns for metabolic disorders began in the 1960s [28], and archived residual newborn DBS have been used as an innovative resource for assessing certain environmental exposures [29, 30]. In a previous study, we explored this resource for retrospective analysis of heavy metals (As, Cd, Hg, and Pb) but found that the standard blood collection cards (i.e., Whatman 903 Protein Saver cards) contain significant and variable background contamination for these elements [31]. To address this challenge, here we present two distinct approaches to 1) investigate the use of archived existing DBS samples for inferring systemic heavy metals exposure (retrospective studies), and 2) interpret the improvement in results that might be achieved with pre-cleaned blood collection cards designed specifically for collecting samples for metals analysis (prospective studies).

METHODS

Blood collection and human participants. Eighty-two children from infancy to age 21 were recruited from the Anne and Robert H. Lurie Children's Hospital of Chicago (formerly Children's Memorial Hospital of Chicago) to participate in our study. Children were recruited and consented during regularly scheduled hospital visits, and volumes of blood that had already been drawn from each child were verified to ensure that no monthly draw limits were approached. Once consented, 5 mL of venous blood was collected by a phlebotomist in 7 mL metal-free vacutainers with EDTA as an anticoagulant and the tubes were gently inverted 8-10 times to ensure proper mixing. In addition, finger-stick DBS samples were collected at the time of phlebotomy by pricking the child's middle or ring finger using sterile single-use micro-lancets. Five drops of blood were collected on Whatman #903 Protein Saver cards, and the specimens were allowed to dry uncovered at room temperature for a minimum of 4 hours. DBS samples were then placed in plastic bags with desiccants, and all blood samples were stored at −20° C. prior to shipment to Northwestern University. Once received in the laboratory all samples were frozen at −80° C. until assayed. This study was reviewed and approved by the Northwestern Institutional Review Board.

Treatment of blood collection cards to remove metal contamination. Five one-inch wide strips of Whatman #903 Protein Saver cards were removed using ceramic scissors (part number, VWR, Atlanta, Ga.) that were washed in 5% acetic acid (v/v) solution prior to use. The excised strips of filter paper, each containing five circular blood collection guidelines, were placed in a 1 L Nalgene metal-free bottle (Fisher Scientific, Pittsburgh, Pa.) containing 5% ultrapure grade nitric acid and 5% ultrapure grade hydrochloric acid (Sigma Aldrich, St. Louis, Mo.) in 18.2 mΩ deionized water. The filter paper strips were incubated for 90 minutes at room temperature on a shaker table at 200 rpm. The solution was then decanted from the bottle, and the bottle was filled with 1 L of 18.2 mΩ deionized water, and incubated for an additional 15 minutes, then followed by two additional water rinses. The cleaned filter paper strips were then removed using acid-washed Teflon tweezers and were dried overnight at room temperature.

Spiked venous blood on DBS cards. Forty previously-frozen whole venous blood samples were randomly selected from the initial 82 and were spotted onto pre-cleaned and untreated strips of Whatman #903 filter paper in 60 µL aliquots. The strips were suspended horizontally above the laboratory bench top and were covered with 4 L beakers to protect the samples from contamination. The blood was dried for four hours at room temperature, and then transferred to trace-metal Nalgene plastic bags (Fisher Scientific, Pittsburgh, Pa.) and stored at −80° C. until assayed. We recognize the distribution of blood across the filter paper may have been altered due to cells being lysed during the freezing process. However, this did not impact our ability to estimate blood volumes since volumes were based on excising entire blood spots, as opposed to punches of blood that have assumed blood volumes.

DBS sample processing. DBS samples were extracted using the procedure described by Funk et al. [31], with minor modifications. In short, entire DBS specimens were excised with acid-washed ceramic scissors using the printed circles on the blood collection cards as a guide. The volume of blood in an intact DBS is approximately 60 µL. However, to account for blood volume variation between samples, the dried mass of each sample was normalized to the mean mass of all of the excised samples using previously described methods [31]. A similar approximate size of a blank filter paper was excised from each card near each blood sample to evaluate background metal contamination in the filter paper. The mass of each blank was also normalized to the mean mass of all of the excised blanks. DBS and filter paper blanks were weighed in 15 mL metal-free polypropylene centrifuge tubes (VWR, Atlanta, Ga.). An extraction solution was prepared using 5% ultrapure grade acetic acid and 0.01% ultrapure grade Triton X-100 (Fisher Scientific, Pittsburgh, Pa.) in 18.2 mΩ deionized water. Two hundred ppb of Au was added to amalgamate Hg and prevent analyte loss throughout the procedure (Inorganic Ventures, Christiansburg, Va.), and five ppb of indium, bismuth, and yttrium were added to the extraction solution as internal standards (Inorganic Ventures, Christiansburg, Va.). Approximately 1.5 mL of extraction solution was then added directly to each vial and the accurate volumes of the extraction solutions were determined by mass. DBS samples and filter paper blanks were then centrifuged at 3600×g for 2 minutes and incubated for 90 minutes at room temperature on a shaker table at 300 rpm. Prior to analysis the centrifuge tubes were inverted and manipulated to adhere the filter paper to the side of the tubes in order to remove them from the blood extracts.

Venous blood processing. Using acid washed pipette tips, 50 µL of venous whole blood was spiked directly into 15 mL metal-free polypropylene centrifuge tubes containing 1.5 mL of extraction solution (described above). The blood extracts were then centrifuged at 3600×g for 2 minutes and incubated for 90 minutes at room temperature on a shaker table at 300 rpm.

Phase 1: DBS vs. whole venous blood (retrospective applications). Eighty-two matched finger stick DBS (i.e., standard DBS cards) and whole venous blood samples were evaluated for potential use for retrospective analysis, that is, using cards previously collected without special procedures for removing background metals. The samples were individually matched as measurements of blank filter paper, DBS, and venous whole blood; they were processed to determine the geometric mean (GS) and geometric standard deviation (GSD) for each metal to characterize their lognormal distributions. The DBS data were individually corrected (subtracted) with their respective blank values for each metal. Standard percentile values were directly observed from tabulated data, and subsequently, scatterplots and regressions were evaluated for association between the "gold standard" venous blood and DBS samples. Correlations between venous blood and DBS samples were evaluated with and without blank background subtraction.

Phase 2: DBS sampling using pre-cleaned vs. untreated blood collection cards (prospective applications). Whole venous blood spotted onto 40 matched pre-cleaned and untreated Whatman #903 filter strips were extracted and analyzed to assess the potential for using DBS sampling in prospective studies specifically designed for heavy metal analysis. Here, one set of cards was preprocessed to remove pre-existing metals contamination to provide a uniformly clean substrate. Scatterplots and regressions were evaluated for association between the pre-cleaned and untreated DBS samples.

Mass spectrometry. Concentrations of As, Pb, Hg, and Cd were quantified using a Thermo Fisher X Series II Inductively Couple Plasma Mass Spectrometer (ICP-MS). Metal concentrations were determined using a five-point calibration curve for each analyte. For Pb, three isotopes were measured and summed (m/z: 206, 207, and 208). Arsenic, Hg, and Cd, were quantified using single isotopes with m/z of 75, 202, and 111, respectively. In addition to the samples and paired card blanks, quality control samples were run along with each batch, consisting of a matrix blank, a trace element whole blood reference (Clin Chek, Munich, Germany), and a trace element whole blood reference spiked onto Whatman #903 filter paper.

Statistics and graphing. Measurement data were organized using MS Excel® spreadsheet software (Microsoft Corp., Redmond, Wash.); statistical analyses and graphing were performed using both Excel and Graph Pad Prism (Graph Pad Software, Inc., La Jolla, Calif.). All data sets were individually examined for summary statistics (mean, standard deviation, median and coefficient of variation) and characterized as exhibiting lognormal distribution (32). The few below detection limit (BDL) values were imputed using the limit of detection (LoD) value; this was necessary for 3 of 1134 total measurements.

Results and Discussion

DBS vs. whole venous blood (retrospective applications). Summary statistics for heavy metal concentrations (in ppb) from blank cards, venous whole blood samples, DBS and background corrected DBS values are provided in Table 1. The geometric mean (GM) and geometric standard deviation (GSD) are calculated under the assumption of lognormal distribution [32]; the remaining statistics are strictly observational; that is, no particular underlying distributions are assumed. Entries of "<LoD" indicate that the value is below the level of detection, entries with "-" occurring for the blank corrected (subtracted) DBS were negative. Due to individual zero or negative values, certain GM entries (As blanks, Cd blood, and all DBS corr.) were estimated by the observed median, rather than from direct calculation of log-transformed data (Table 1).

These summary data indicate that the whole blood and DBS method yield similar trends, but with noticeable mean level offsets presumably stemming from background metal concentrations inherent to the filter paper matrix. While use of pair-wise blank subtraction did not significantly improve results (described below), taken as groups, it is probably reasonable to apply a group "blank" correction.

Individual samples evaluation. We found that blank correction at the individual sample level is not particularly helpful. This observation is attributed to large spot-to-spot heterogeneity in background contamination within cards. In fact, there seems to be additional biasing effects from the cards occurring beyond random contamination, for which we have no explanation. FIGS. 10-13 show the direct comparisons between venous blood levels (x-axis) vs. finger stick DBS samples (y-axis), with and without individual background correction.

TABLE 1

Summary statistics: Group-wise comparison of metal species and sample format; all DBS measurements are from standard Whatman #903 cards (n = 82/group).

| Metal Species | Sample | GM | GSD | Min | 5th % | 25th % | 50th % | 75th % | 95th % | Max |
|---|---|---|---|---|---|---|---|---|---|---|
| As (ppb) | Blanks | 0.05 | 6.68 | <LoD | <LoD | <LoD | 0.05 | 0.66 | 1.08 | 2.61 |
| | Blood | 8.83 | 1.18 | 6.03 | 6.81 | 7.96 | 8.94 | 9.70 | 11.12 | 16.28 |
| | DBS | 9.40 | 2.21 | <LoD | 5.75 | 6.89 | 8.25 | 11.24 | 30.39 | 50.95 |
| | DBS Corr. | 7.97 | 2.26 | 0.00 | 5.18 | 6.58 | 7.97 | 11.02 | 30.36 | 50.95 |
| Cd (ppb) | Blanks | 0.14 | 1.43 | <LoD | 0.05 | 0.12 | 0.13 | 0.16 | 0.24 | 0.65 |
| | Blood | 0.10 | 1.85 | <LoD | 0.00 | 0.05 | 0.10 | 0.15 | 0.28 | 0.48 |
| | DBS | 0.32 | 2.73 | <LoD | 0.12 | 0.18 | 0.29 | 0.48 | 1.52 | 2.71 |
| | DBS Corr. | 0.14 | 3.98 | — | — | 0.05 | 0.14 | 0.32 | 1.37 | 2.71 |
| Hg (ppb) | Blanks | 0.10 | 2.43 | 0.04 | 0.04 | 0.05 | 0.09 | 0.16 | 0.37 | 2.86 |
| | Blood | 0.45 | 1.97 | 0.13 | 0.15 | 0.28 | 0.45 | 0.69 | 1.40 | 2.10 |
| | DBS | 0.53 | 1.66 | <LoD | 0.25 | 0.35 | 0.51 | 0.72 | 1.20 | 8.04 |
| | DBS Corr. | 0.36 | 1.99 | — | 0.04 | 0.26 | 0.36 | 0.59 | 1.11 | 5.17 |
| Pb (ppb) | Blanks | 1.89 | 3.18 | 0.02 | 0.75 | 1.08 | 1.58 | 3.14 | 10.55 | 41.88 |
| | Blood | 6.32 | 1.81 | 2.38 | 2.91 | 4.03 | 5.70 | 8.56 | 20.17 | 30.45 |
| | DBS | 11.01 | 2.19 | <LoD | 4.39 | 5.84 | 9.44 | 19.15 | 34.14 | 122.76 |
| | DBS Corr. | 6.80 | 2.67 | — | — | 3.19 | 6.60 | 16.82 | 33.14 | 122.00 |

Visual inspection of the scatterplots shows that the relationship between the accepted blood measurement and the corresponding measurement in DBS samples is not much improved by within-card background correction. However, slopes are positive with statistical significance for all four metals indicating that there are indeed positive correlations between venous blood and DBS measurements. Table 2 shows these results as calculated in log space. Slopes are all less than 1.0; we attribute this to positive bias at lower absolute blood concentrations. The p-values for the slopes as different from zero are highly significant; however, as is obvious from the scatterplots, the r2 values demonstrate that there is appreciable scatter in the data.

These results demonstrate that there is little value in correcting individually for metals background as these levels are highly variable within a card. The best we could accomplish would be a form of blanket statistical subtraction for all cards that would show only statistically valid exceedances beyond the highest overall background levels. Such retrospective approaches will be explored in future work.

DBS sampling using pre-cleaned vs. untreated blood collection cards (prospective applications). The focus of this part of the investigation was to determine if the background confounding could be resolved by pre-cleaning filter paper before use. Certainly, this is only possible for prospective type studies, where the cards can be treated before the blood is collected. We used 40 venous blood samples from individuals to test the pre-cleaning method; again, the results from venous blood analyses were considered the accepted "gold standard" values, and were compared to the standard DBS samples and the DBS samples that were spotted onto pre-cleaned cards. Table 3 shows the summary evaluation of these results (analogous to the Table 1 results). Here we see that the summary and percentile statistics are much more aligned between the cleaned DBS substrate and the venous blood values (Table 3).

These summary data indicate an across the board improvement in linking DBS and venous blood metals content when using pre-cleaned cards, especially for Hg and Pb. Taken as a group, there is no obvious (qualitative) bias.

Individual samples evaluation. As in the retrospective analysis section, it is important to assess the comparisons of the prospective data at the individual samples level. Again, we show the scatterplots, this time between the venous blood analyses (x-axis) and the measurements of the DBS samples from the pre-cleaned cards (y-axis).

TABLE 2

Summary statistics for scatterplot slopes of association between venous blood measurements and DBS measurements from standard Whatman #903 cards (n = 82/group).

| Metal Species | Compare | Slope | p-value | $r^2$ | sig. pos. |
|---|---|---|---|---|---|
| As | Blood vs. DBS | 0.983 | 0.009 | 0.063 | yes |
| | Blood vs. DBS corr | 0.89 | 0.022 | 0.065 | yes |
| Cd | Blood vs. DBS | 0.392 | <0.001 | 0.186 | yes |
| | Blood vs. DBS corr | 0.698 | 0.002 | 0.134 | yes |
| Hg | Blood vs. DBS | 0.602 | <0.001 | 0.498 | yes |
| | Blood vs. DBS corr | 0.872 | <0.001 | 0.575 | yes |
| Pb | Blood vs. DBS | 0.594 | <0.001 | 0.022 | yes |
| | Blood vs. DBS corr | 0.704 | <0.001 | 0.187 | yes |

TABLE 3

Summary statistics: Group-wise comparison of metal species and sample format; DBS measurements are from standard DBS samples, and from DBS samples collected on pre-cleaned cards; "Blood" refers to venous blood measurements (n = 40/group).

| Metal Species | Sample | GM | GSD | Min | 5th % | 25th % | 50th % | 75th % | 95th % | Max |
|---|---|---|---|---|---|---|---|---|---|---|
| As (ppb) | DBS orig | 5.68 | 2.68 | <LoQ | 20 | 2.77 | 7.16 | 10.94 | 16.73 | 19.02 |
| | DBS clean | 7.48 | 154 | 0.9 | 5.01 | 6.73 | 7.76 | 8.96 | 11.11 | 17.83 |
| | Blood | 9.1 | 139 | 3.6 | 594 | 7.52 | 9.73 | 11.1 | 12.79 | 24 |
| Cd (ppb) | DBS orig | 0.09 | 1.8 | 0.12 | 0.15 | 0.18 | 0.23 | 0.27 | 0.45 | 0.9 |
| | DBS clean | 0.09 | 1.77 | <LoQ | 0.03 | 0.05 | 0.08 | 0.11 | 0.113 | 0.43 |
| | Blood | 0.09 | 1.8 | 0.03 | 0.05 | 0.08 | 0.08 | 0.13 | 0.2 | 0.5 |

TABLE 3-continued

Summary statistics: Group-wise comparison of metal species and sample format; DBS measurements are from standard DBS samples, and from DBS samples collected on pre-cleaned cards; "Blood" refers to venous blood measurements (n = 40/group).

| Metal Species | Sample | GM | GSD | Min | 5$^{th}$ % | 25$^{th}$ % | 50$^{th}$ % | 75$^{th}$ % | 95$^{th}$ % | Max |
|---|---|---|---|---|---|---|---|---|---|---|
| Hg (ppb) | DBS orig | 2.41 | 1.44 | 1.68 | 1.68 | 1.92 | 2.22 | 2.74 | 3.85 | 11.82 |
| | DBS clean | 0.59 | 1.76 | 0.18 | 25 | 0.4 | 0.63 | 0.81 | 1.49 | 1.9 |
| | Blood | 0.43 | 224 | 0.08 | 0.13 | 0.23 | 0.44 | 0.73 | 1.65 | 1.98 |
| Pb (ppb) | DBS orig | 8.2 | 1.6 | 3.42 | 428 | 6.32 | 759 | 11.42 | 16.83 | 30.54 |
| | DBS clean | 5.22 | 1.71 | 2.3 | 255 | 3.49 | 496 | 6.43 | 13.32 | 26.48 |
| | Blood | 5.98 | 1.66 | 2.6 | 3.02 | 4.03 | 5.63 | 7.69 | 13.66 | 30.18 |

These scatterplots using pre-cleaned cards demonstrate a marked improvement over their counterparts in the previous section using standard DBS collected on untreated cards. We note that there is a slight bias in the slopes below 1.0, which could be perceived as a small sink for trace metals created by the acid wash process. This is pure speculation; it is also possible that this is an artifact of linear regression of data that should have been log-transformed or a few influential outliers. Regardless, the cleaned cards provide a significant improvement and could be used effectively as a surrogate for venous whole blood analysis.

In the Table 3 below, we present the slope factor results comparing the linear regressions as drawn in FIGS. 14-17, and the presumed more robust slopes calculated in log-log space. The results are equivocal, with some slight improvement in slope comparisons for As, Cd, and Pb (Table 4).

Predicting blood concentrations from DBS. If we concede that the log-transformed regressions are slightly more robust in dealing with influential outliers, then we can estimate the concentration in the blood ($C_{blood}$) in terms of the measured value from the pre-cleaned DBS samples and the regression coefficients as:

$$C_{blood}(DBS) = \exp\{[ln(DBS) - b']/m'\} \quad (1)$$

where m'=slope and b'=intercept are the regression coefficients of the log-transformed data, analogous to the regressions performed using the raw data in FIGS. 14-17. One could also use the linear regressions from those figures in a standard calibration application in this format:

$$C_{blood}(DBS) = (DBS - b)/m \quad (2)$$

where m and b are the slope and intercept coefficients from the natural space regressions. The choice of regression space is not obvious. If there are large influential outliers, then log-space is preferable, if however, there are many very low-level imputed values, they skew the low end unnecessarily and linear regression yields a more practical result.

The next step is to estimate the variability between the standard method (venous blood analysis) and the pre-cleaned DBS sampling method. Although we might designate the venous blood method to be the default, it too is subject to some level of variability, and so we need to make a decision as to how to interpret the comparisons. There are two paths: pronounce that the variability in the venous blood measurements is negligible (gold standard), or assume that we do not know and treat each method equally with respect to variance. A second decision is how to couch the results; we can either state error in terms of percent with respect to the concentration, or make a blanket statement of confidence limit across all levels. Either is acceptable, often the percent method is preferable as it is easier to compare disparate data, in our case, across different metal species. Table 5 shows the results from this regression exercise for both approaches.

The table demonstrates that the choice of prediction space is equivocal. The one anomaly is the slope/intercept for the prediction of As, where there is some clustering (see the scatterplot in FIG. 14) that appears to shift the slope a bit. Overall, the scatter between the two methods has a prediction band error ranging from ±21% to ±76%. This is not as dire as it initially appears. Consider for example that a DBS measurement of as at the median of 7.16 ppm would indicate a blood level between 4.3 and 10.0 ppm with 95% confidence. Also, we need to consider that the venous blood levels are subject to error. As such, the relationship between cleaned DBS samples and venous blood measurements is useful for using one or the other.

TABLE 4

Summary statistics for scatterplot slopes of association between venous blood measurements and DBS measurements from DBS collected on pre-cleaned cards (n = 40/group), in both linear and log-transformed data regressions.

| Metal Species | Compare | Slope | p-value | $r^2$ | sig. pos. |
|---|---|---|---|---|---|
| As | Blood vs. DBS (lin.) | 0.654 | <0.0001 | 0.682 | yes |
| | Blood vs. DBS (log) | 1.003 | <0.0001 | 0.58 | yes |
| Cd | Blood vs. DBS (lin.) | 0.861 | <0.0001 | 0.861 | yes |
| | Blood vs. DBS (log) | 0.916 | <0.0001 | 0.858 | yes |
| Hg | Blood vs. DBS (lin.) | 0.831 | <0.0001 | 0.892 | yes |
| | Blood vs. DBS (log) | 0.568 | <0.0001 | 0.658 | yes |
| Pb | Blood vs. DBS (lin.) | 0.844 | <0.0001 | 0.94 | yes |
| | Blood vs. DBS (log) | 1.033 | <0.0001 | 0.956 | yes |

TABLE 5

Prediction band results from calibrated "clean" DBS vs. venous blood regressions in linear and log-space.

| Metal Species | Prediction Model | slope (m) | intercept (b) | $r^2$ | % error (+/−) |
|---|---|---|---|---|---|
| As | Blood vs. DBS (lin.) | 1.000 | −0.001 | 0.6819 | 47.6 |
| | Blood vs. DBS (log) | 0.793 | 2.131 | 0.6186 | 38.8 |
| Cd | Blood vs. DBS (lin.) | 0.997 | −0.003 | 0.9498 | 50.5 |
| | Blood vs. DBS (log) | 1.045 | −0.005 | 0.9535 | 40.2 |
| Hg* | Blood vs. DBS (lin.) | 1.000 | −0.004 | 0.8921 | 76.5 |
| | Blood vs. DBS (log) | 1.083 | −0.040 | 0.9113 | 62.7 |
| Pb | Blood vs. DBS (lin.) | 1.000 | −0.001 | 0.9399 | 21.5 |
| | Blood vs. DBS (log) | 0.997 | 0.076 | 0.9393 | 21.2 |

*5 low-level imputed values removed

CONCLUSIONS

Dried blood spots are proposed as a non-invasive and even self-administered alternative to sampling whole venous blood. The retrospective data from standard DBS cards are not suitable for metals analysis as they exhibit too much heterogeneity of background. However, all standard DBS measurements demonstrate a positive slope with respect to matched venous blood samples suggesting that there is at least some statistical, albeit noisy, relationship. It is possible to investigate this behavior in more detail with further measurements of the spatial heterogeneity within cards, and the population heterogeneity between cards.

Using pre-cleaned cards for prospective (non-invasive) sampling has promise. Based on these limited samples, we find excellent linearity for groups of samples, and that a single DBS sample can provide a bounded and useful estimate for the "true" blood level as illustrated in Table 5.

REFERENCES

1. Harper M, Weis C, Pleil J D, Blount B C, Miller A, et al. (2015) Commentary on the contributions and future role of occupational exposure science in a vision and strategy for the discipline of exposure science. Journal of exposure science and environmental epidemiology 25: 381-387.
2. Pleil J D, Blount B C, Waidyanatha S, Harper M (2012) Establishing exposure science as a distinct scientific discipline. J Expo Sci Environ Epidemiol 22: 317-319.
3. Bean H D, Pleil J D, Hill J E (2015) Editorial: new analytical and statistical approaches for interpreting the relationships among environmental stressors and biomarkers. Biomarkers 20: 1-4.
4. Rappaport S M, Smith M T (2010) Epidemiology. Environment and disease risks. Science 330: 460-461.
5. Wild C P (2005) Complementing the genome with an "exposome": the outstanding challenge of environmental exposure measurement in molecular epidemiology. Cancer epidemiology, biomarkers and prevention 14: 1847-1850.
6. Pleil J D, Sheldon L S (2011) Adapting concepts from systems biology to develop systems exposure event networks for exposure science research. Biomarkers 16: 99-105.
7. Sobus J R, Tan Y M, Pleil J D, Sheldon L S (2011) A biomonitoring framework to support exposure and risk assessments. Sci Total Environ 409: 4875-4884.
8. Tan Y M, Sobus J, Chang D, Tornero-Velez R, Goldsmith M, et al. (2012) Reconstructing human exposures using biomarkers and other "clues". J Toxicol Environ Health B Crit Rev 15: 22-38.
9. Park H A (2013) The Korea national health and nutrition examination survey as a primary data source. Korean J Fam Med 34: 79.
10. Sobus J R, DeWoskin R S, Tan Y M, Pleil J D, Phillips M B, et al. (2015) Uses of NHANES biomarker data for chemical risk assessment: Trends, challenges, and opportunities. Environmental Health Perspectives.
11. Canadian Health Measures Survey 2015.
12. German Environmental Survey 2015.
13. Demetriou C A, Vineis P (2015) Carcinogenicity of ambient air pollution: use of biomarkers, lessons learnt and future directions. J Thorac Dis 7: 67-95.
14. Miller M G (2007) Environmental metabolomics: A SWOT analysis (strengths, weaknesses, opportunities, and threats). J Proteome Res 6: 540-545.
15. Pleil J D (2012) Categorizing biomarkers of the human exposome and developing metrics for assessing environmental sustainability. J Toxicol Environ Health B Crit Rev 15: 264-280.
16. Sørensen M, Autrup H, Møller P, Hertel O, Jensen S S, et al. (2003) Linking exposure to environmental pollutants with biological effects. Mutat Res 544: 255-271.
17. Barbee J Y Jr, Prince T S (1999) Acute respiratory distress syndrome in a welder exposed to metal fumes. South Med J 92: 510-512.
18. Seidal K, Jörgensen N, Elinder C G, Sjögren B, Vahter M (1993) Fatal cadmium-induced pneumonitis. Scand J Work Environ Health 19: 429-431.
19. Behbahani M, Tapeh N A G, Mahyari M, Pourali A R, Amin B G, et al. (2014) Monitoring of trace amounts of heavy metals in different food and water samples by flame atomic absorption spectrophotometer after preconcentration by amine-functionalized graphene nano sheet. Environ Monit Assess 186: 7245-7257.
20. Roychowdhury T, Tokunaga H, Ando M (2003) Survey of arsenic and other heavy metals in food composites and drinking water and estimation of dietary intake by the villagers from an arsenic-affected area of West Bengal, India. Sci Total Environ 308: 15-35.
21. Zheng J, Chen K H, Yan X, Chen S J, Hu G C, et al. (2013) Heavy metals in food, house dust, and water from an e-waste recycling area in South China and the potential risk to human health. Ecotoxicol Environ Saf 96: 205-212.
22. Jarup L (2003) Hazards of heavy metal contamination. Br Med Bull. 68:167-182.
23. Al-Saleh I, Shinwari N, Mashhour A, Mohamed Gel D, Rabah A (2011) Heavy metals (lead, cadmium and mercury) in maternal, cord blood and placenta of healthy women. Int J Hyg Environ Health 214: 79-101.
24. Pigatto P D, Minoia C, Ronchi A, Guzzi G (2013) Human placenta and markers of heavy metals exposure. Environ Health Perspect 121: A10.
25. Roels H, Hubermont G, Buchet J P, Lauwerys R (1978) Placental-transfer of lead, mercury, cadmium, and carbon-monoxide in women III. Factors influencing accumulation of heavy-metals in placenta and relationship between metal concentration in placenta and in maternal and cord blood. Environ Res. 16: 236-247.
26. Davit C J, Hundley R J, Bacic J D, Hanson E M (2011) A pilot study to improve venipuncture compliance in children and adolescents with autism spectrum disorders. J Dev Behav Pediatr 32: 521-525.
27. McDade T W, Williams S, Snodgrass J J (2007) What a drop can do: dried blood spots as a minimally invasive method for integrating biomarkers into population-based research. Demography 44: 899-925.
28. Guthrie R, Susi A (1963) A simple phenylalanine method for detecting phenylketonuria in large populations of newborn infants. Pediatrics 32: 338-343.
29. Olshan A F (2007) Meeting report: the use of newborn blood spots in environmental research: opportunities and challenges. Environ Health Perspect 115: 1767-1779.
30. Funk W E, Waidyanatha S, Chaing S H, Rappaport S M (2008) Hemoglobin adducts of benzene oxide in neonatal and adult dried blood spots. Cancer Epidemiol Biomarkers Prev 17: 1896-1901.
31. Funk W E, McGee J K, Olshan A F, Ghio A J (2013) Quantification of arsenic, lead, mercury and cadmium in newborn dried blood spots. Biomarkers 18: 174-177.
32. Pleil J D, Sobus J R, Stiegel M A, Hu D, Oliver K D, et al. (2014) Estimating common parameters of log normally distributed environmental and biomonitoring data: har- Example 3—A Heavy Metal Blood Collection Card for Screening Newborns and Children Reference is made to the Invention Disclosure Form entitled "A Heavy Metal Blood Collection Card for Screening Newborns and Children," by William E. Funk, Thomas W. McDade, and Andrew Unger, received date of Apr. 27, 2016.

Abstract

Heavy metals, including arsenic (As), lead (Pb), mercury (Hg), and cadmium (Cd), are ubiquitous environmental toxicants listed as the $1^{st}$, $2^{nd}$, $3^{rd}$, and $7^{th}$ most important hazardous chemicals on the 2011 CERCLA priority list of 275 substances, respectively. Heavy metals can be quantified in blood to estimate environmental exposures. However, the requirement for venous blood, which is costly, invasive, and must be collected by a trained phlebotomist, is an obstacle for assessing heavy metal exposures. This is especially the case with pediatric populations and younger children, for whom the developmental consequences of heavy metal exposure can be particularly severe. Dried blood spots (DBS)—drops of whole blood collected on filter paper following a simple finger of heel prick—are a "field friendly" alternative to venous blood collection for assessing exposures to heavy metals. However, filter papers used to collect DBS samples (e.g., Whatman #903 Protein Saver Cards) are not designed for trace-level heavy metals analysis, and background contamination in the filter paper interferes with quantification of heavy metals in DBS samples leading to imprecise estimates of exposure. To address this challenge, we have developed a DBS specimen collection device that is optimized for quantifying trace-level heavy metals in blood.

Applications and Advantages

The disclosed DBS specimen collection device may have a number of applications, which may include but are not limited to: i) Newborn heavy metals screening; ii) Pediatric heavy metal screening; iii) Population-based heavy metal screening; and iv) At-home heavy metal screening. The disclosed DBS specimen collection device may have a number of advantages, which may include but are not limited to: i) Minimally-invasive; ii) Built-in desiccant to absorb water during drying and prevent contamination; iii) High analytical precision due to removal of metal contamination and metal free; surfaces inside collection card; iv) Field-friendly; v) Designed specifically to attach as an add-on to newborn screening cards; vi) Can be sent via standard US mail at room temperature; vii) Easy to store in laboratory using minimal storage space; and viii) Bar coded for sample identification (can be linked with newborn screening bar code).

Description

The disclosed DBS specimen collection device may be further described by referring to FIGS. 18-21. As indicated in FIGS. 18A and 18B, the device includes a support card that is folded and is present in a sealed plastic bag enclosure. The sealed plastic bag enclosure may include a desiccant to absorb undesired moisture. The sealed plastic bag enclosure ensures that the device remains dry and uncontaminated prior to use.

One side of the device may be imprinted with branding and the other side of the device may include a tag, such as a bar code for identifying/tracking the device and any blood sample contained thereon. The tag may be scanned through the sealed plastic bag enclosure, for example, when the sealed plastic bag enclosure is clear. The sealed plastic bag enclosure includes an adhesive strip for adhering the sealed plastic bag to another support, such as an add-on to a standard newborn screening card. (See FIG. 19A,B.)

Figure 20B:
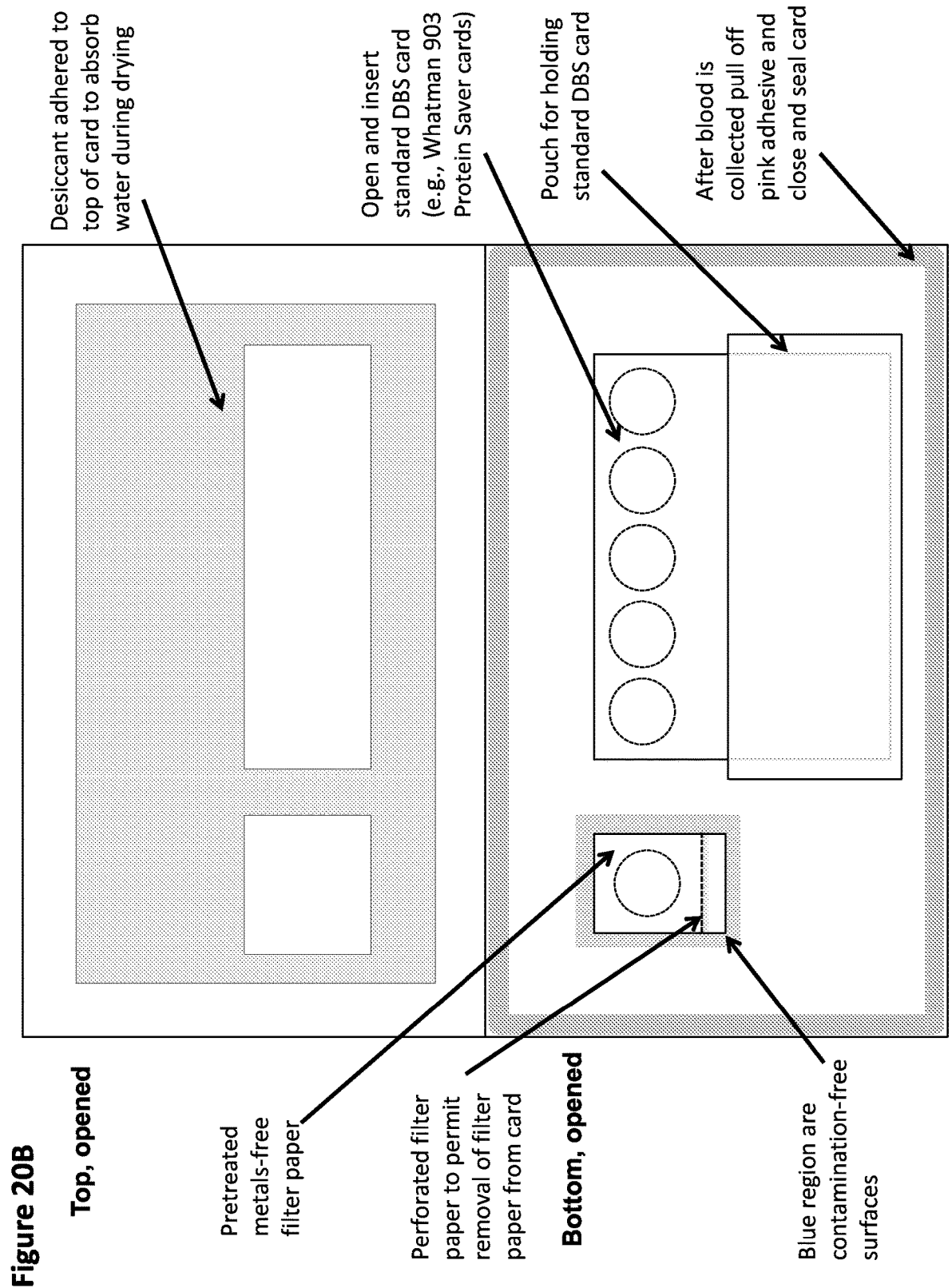
Figure 21B:
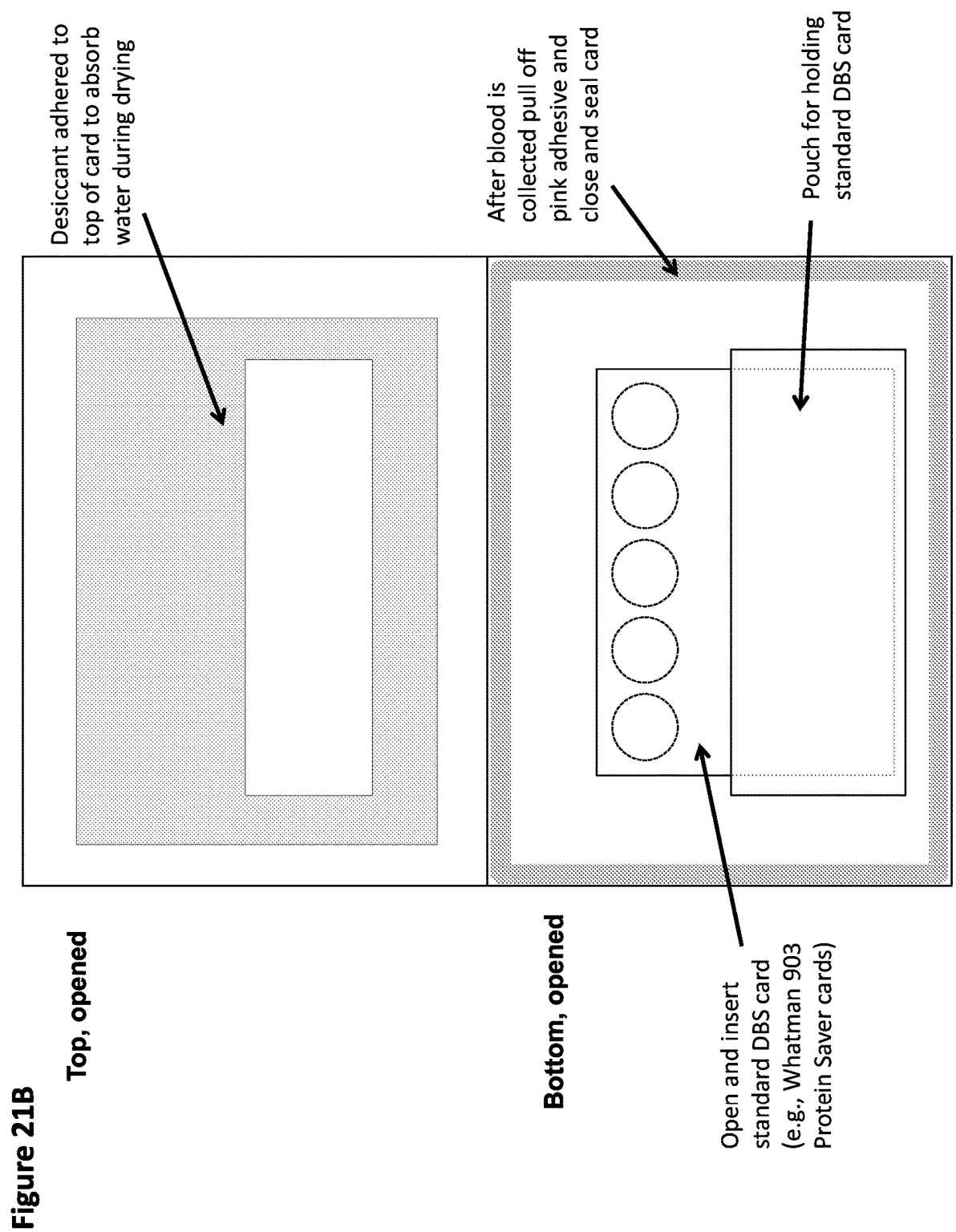

When a user is ready to collect a blood sample, a perforated end of the sealed plastic bag enclosure may be torn to remove the device. The device then may be unfolded as illustrated in FIGS. 20A,B and 21A,B. The unfolded device includes a front side to which a desiccant is adhered. In addition, a pre-treated metals-free filter paper is adhered to a metal free surface of the support card. The filter paper may be perforated to facilitate removal of the paper from the support card at the time that the blood sample is to be processed. The front surface of the support card may include an adhesive such that when the support card is refolded, the adhesive will seal the desiccant and filter paper with blood sample on the inside of the folded support card. The outside of the folded card includes the tag for identifying/tracking the device and blood sample.

Features

The disclosed DBS specimen collection device may have a number of applications, which may include but are not limited to: (1) a sealed enclosure to protect the desiccant from absorbing water from the air prior to blood collection, (2) a bar code for tracking samples that can be scanned without opening the sealed enclosure, (3) a bar code that can be linked to newborn screening card bar code, (4) a pull away adhesive strip for attaching the add-on heavy metals newborn blood collection card to standard newborn screening cards, (5) a perforation to permit the sealed bag to be opened and removed from the standard newborn screening card at the time of blood collection, (6) a unique sample ID printed outside and inside the card, (7) pretreated filter paper to remove background contamination, (8) an attached desiccant to absorb water during drying and to prevent contamination after blood collection, (9) a metals-free surface below and above where blood in applied, (10) a pull away adhesive strip for sealing the card after blood collection, (11) a perforation to permit filter paper to be easily removed form the card at the time of analysis, (12) a perforation to permit the removal of the sample from the filter paper (or can use a metal-free blood punch if not using entire spot for the analysis), (13) minimum card dimensions for optimal storage.

CONCLUSION

The disclosed heavy metal newborn blood collection card permits blood to be collected using a simple and minimally-invasive heel prick. The card is designed as an add-on to attach to conventional newborn screening cards used by all states in the US and many other countries. Heavy metal exposures are a critical concern during early development. This innovation allows for heavy metals to be accurately measured in blood during the time of routine newborn screening (i.e., no additional heel prick is required). Knowledge of heavy metal exposures around the time of birth can facilitate remediation to reduce additional exposures during critical periods of infant/child development.

The blood collection device will also be useful for school- or community-based screening of children, to identify children at risk of adverse developmental consequences following heavy metal exposures (e.g., Flint, Mich.). The alternative approach, using venipuncture blood, is more expensive, and cannot be implemented in schools or communities, and therefore limits screening.

The collection cards also may be used for collecting other body fluids with diagnostic utility (e.g., urine, saliva, breast milk) that can be applied to the filter paper with a pipettor. After application to filter paper, the samples may be dried and protected from contamination during transport and storage within the sealed collection system.

The collection cards also may be useful for collecting blood in space, to monitor environmental exposures and health of humans and experimental animals, for screening and research purposes, for example where the alternative approach, using venipuncture blood, is not feasible because of the need to centrifuge the sample prior to storage. In a zero-gravity environment, the force of centrifugation can impact the course and stability of space craft. Centrifuges are also heavy, and take up valuable cargo room, as do freezers, which are required to preserve venous blood samples.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for determining the approximate venous concentration of one or more heavy metals selected from As, Pb, Hg, Cd, and combinations thereof in a subject; the method comprising the steps of:
   a) applying a whole blood sample from a skin prick of the subject to a treated sample pad that is free of detectable levels of heavy metals or comprises less than about 5 ng of the heavy metals;
   b) extracting the whole blood sample from the sample pad into an extraction solution that is free of detectable levels of heavy metals or comprises the heavy metals at a concentration of less than 5 ppb, the extraction solution comprising a short-carbon-chain organic acid carboxylic acid;
   c) determining the approximate concentration of the heavy metals in the extraction solution; and
   d) determining the approximate venous concentration of the heavy metals based on the determined approximate concentration of the heavy metals in the extraction solution.

2. The method of claim 1, wherein the whole blood sample has a volume of 50-100 µl.

3. The method of claim 1, wherein the treated sample pad comprises treated cellulose filter paper.

4. The method of claim 1, comprising allowing the applied whole blood sample to dry and form a dried blood spot (DBS) on the sample pad prior to extracting the whole blood sample from the sample pad.

5. The method of claim 1, wherein the extraction solution comprises a non-ionic surfactant.

6. The method of claim 1, wherein step c) is performed using a mass spectrometer.

7. The method of claim 6, wherein the determined concentration of the heavy metals in the extraction solution is in the low parts per trillion (ppt) range.

8. A method for determining the approximate venous concentration of one or more heavy metals selected from As, Pb, Hg, Cd, and combinations thereof in a subject, the method comprising steps of:
   a) applying a whole blood sample from a skin prick of the subject to a treated sample pad that is free of detectable levels of heavy metals or comprises less than 5 ng of the heavy metals;
   b) extracting the whole blood sample from the sample pad into an extraction solution that is free of detectable levels of heavy metals or comprises the heavy metals at a concentration of less than 5 ppb;
   c) determining the approximate concentration of the heavy metals in the extraction solution using a mass spectrometer; and
   d) determining the approximate venous concentration of the heavy metals based on the determined approximate concentration of the heavy metals in the extraction solution.

9. The method of claim 8, wherein the whole blood sample has a volume of 50-100 µl.

10. The method of claim 8, wherein the treated sample pad comprises treated cellulose filter paper.

11. The method of claim 8, comprising allowing the applied whole blood sample to dry and form a dried blood spot (DBS) on the sample pad prior to extracting the whole blood sample from the sample pad.

12. The method of claim 8, wherein the extraction solution comprises a short-carbon-chain organic acid carboxylic acid.

13. The method of claim 8, wherein the extraction solution comprises a non-ionic surfactant.

14. A method for determining the approximate venous concentration of one or more heavy metals selected from As, Pb, Hg, Cd, and combinations thereof in a subject, the method comprising the steps of:
   a) applying a whole blood sample from a skin prick of the subject to a treated sample pad that is free of detectable levels of heavy metals or comprises less than 5 ng of the heavy metals;
   b) extracting the whole blood sample from the sample pad into an extraction solution that is free of detectable levels of heavy metals or comprises the heavy metals at a concentration of less than 5 ppb;
   c) determining the approximate concentration of the heavy metals in the extraction solution using a mass spectrometer, the determined concentration of the heavy metals in the extraction solution being in the low parts per trillion (ppt) range; and
   d) determining the approximate venous concentration of the heavy metals based on the determined approximate concentration of the heavy metals in the extraction solution.

15. The method of claim 14, wherein the whole blood sample has a volume of 50-100 μl.

16. The method of claim 14, wherein the treated sample pad comprises treated cellulose filter paper.

17. The method of claim 14, comprising allowing the applied whole blood sample to dry and form a dried blood spot (DBS) on the sample pad prior to extracting the whole blood sample from the sample pad.

18. The method of claim 14, wherein the extraction solution comprises a short-carbon-chain organic acid carboxylic acid.

19. The method of claim 14, wherein the extraction solution comprises a non-ionic surfactant.

* * * * *